US 11,308,622 B2

(12) United States Patent
Miyasa et al.

(10) Patent No.: US 11,308,622 B2
(45) Date of Patent: Apr. 19, 2022

(54) INFORMATION PROCESSING APPARATUS AND METHOD FOR CONTROLLING THE SAME TO GENERATE A DIFFERENCE IMAGE FROM FIRST AND SECOND INSPECTION IMAGES

(71) Applicant: CANON KABUSHIKI KAISHA, Tokyo (JP)

(72) Inventors: Kazuhiro Miyasa, Narashino (JP); Daisuke Kibe, Utsunomiya (JP); Yukari Nakashoji, Tokyo (JP); Kiyohide Satoh, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/616,184

(22) PCT Filed: May 21, 2018

(86) PCT No.: PCT/JP2018/019538
§ 371 (c)(1),
(2) Date: Nov. 22, 2019

(87) PCT Pub. No.: WO2018/221302
PCT Pub. Date: Dec. 6, 2018

(65) Prior Publication Data
US 2020/0160524 A1    May 21, 2020

(30) Foreign Application Priority Data

May 31, 2017   (JP) .............................. JP2017-108241

(51) Int. Cl.
*G06T 7/00*     (2017.01)
*G16H 30/40*    (2018.01)
*G09G 5/377*    (2006.01)

(52) U.S. Cl.
CPC .......... *G06T 7/0016* (2013.01); *G09G 5/377* (2013.01); *G16H 30/40* (2018.01);
(Continued)

(58) Field of Classification Search
None
See application file for complete search history.

(56) References Cited

U.S. PATENT DOCUMENTS 6,215,893 B1 * 4/2001 Leshem ............... A61B 5/0059
382/128
2001/0002934 A1    6/2001 Oosawa
(Continued)

FOREIGN PATENT DOCUMENTS

JP      2013-126575 A     6/2013
WO     2005/120353 A1    12/2005

*Primary Examiner* — Jeffrey J Chow
(74) *Attorney, Agent, or Firm* — Canon U.S.A., Inc. I.P. Division

(57) ABSTRACT

An information processing apparatus includes an image obtaining unit configured to obtain a first inspection image having first supplemental information and a second inspection image having second supplemental information, a difference image obtaining unit configured to obtain a difference image generated using the first and second inspection images, a difference information obtaining unit configured to obtain difference information on a difference between the first supplemental information and the second supplemental information, and an association unit configured to associate the difference information with the difference image.

18 Claims, 13 Drawing Sheets

(52) U.S. Cl.
CPC ............... *G06T 2207/10081* (2013.01); *G06T 2207/10088* (2013.01); *G06T 2207/20224* (2013.01); *G09G 2380/08* (2013.01)

(56) References Cited

U.S. PATENT DOCUMENTS

| | | | | |
|---|---|---|---|---|
| 2004/0059215 | A1* | 3/2004 | Nishimura | G16H 15/00 600/410 |
| 2004/0081342 | A1* | 4/2004 | Sato | G06T 7/0012 382/128 |
| 2006/0242146 | A1* | 10/2006 | Piacsek | G06T 7/64 |
| 2009/0310843 | A1* | 12/2009 | Moriya | A61B 6/469 382/131 |
| 2011/0170753 | A1* | 7/2011 | Miyasa | G06K 9/3233 382/128 |
| 2013/0170720 | A1* | 7/2013 | Hu | G06K 9/6207 382/131 |
| 2013/0208966 | A1* | 8/2013 | Zhao | G16H 10/60 382/131 |
| 2013/0223708 | A1* | 8/2013 | Fukatsu | G06T 7/0012 382/128 |
| 2014/0063453 | A1* | 3/2014 | Natsuhori | G06T 7/0012 351/206 |
| 2014/0105478 | A1* | 4/2014 | Kasahara | A61B 8/486 382/131 |
| 2014/0161339 | A1* | 6/2014 | Wakai | G06T 7/0012 382/131 |
| 2015/0254836 | A1* | 9/2015 | Sako | A61B 1/04 382/128 |
| 2016/0307341 | A1* | 10/2016 | Sato | A61B 3/0058 |
| 2017/0011509 | A1* | 1/2017 | Ryu | A61B 8/5276 |
| 2017/0148157 | A1* | 5/2017 | Ninomiya | G06T 7/0012 |
| 2017/0243379 | A1* | 8/2017 | Arai | G06T 11/005 |
| 2018/0012354 | A1* | 1/2018 | Fisher | G06F 19/00 |
| 2018/0064422 | A1 | 3/2018 | Otomaru | |
| 2018/0214714 | A1* | 8/2018 | Carpenter | A61N 5/10 |
| 2019/0027252 | A1* | 1/2019 | Calhoun | G06K 9/522 |
| 2019/0108637 | A1* | 4/2019 | Su | G06T 7/0012 |

* cited by examiner

[Fig. 1]
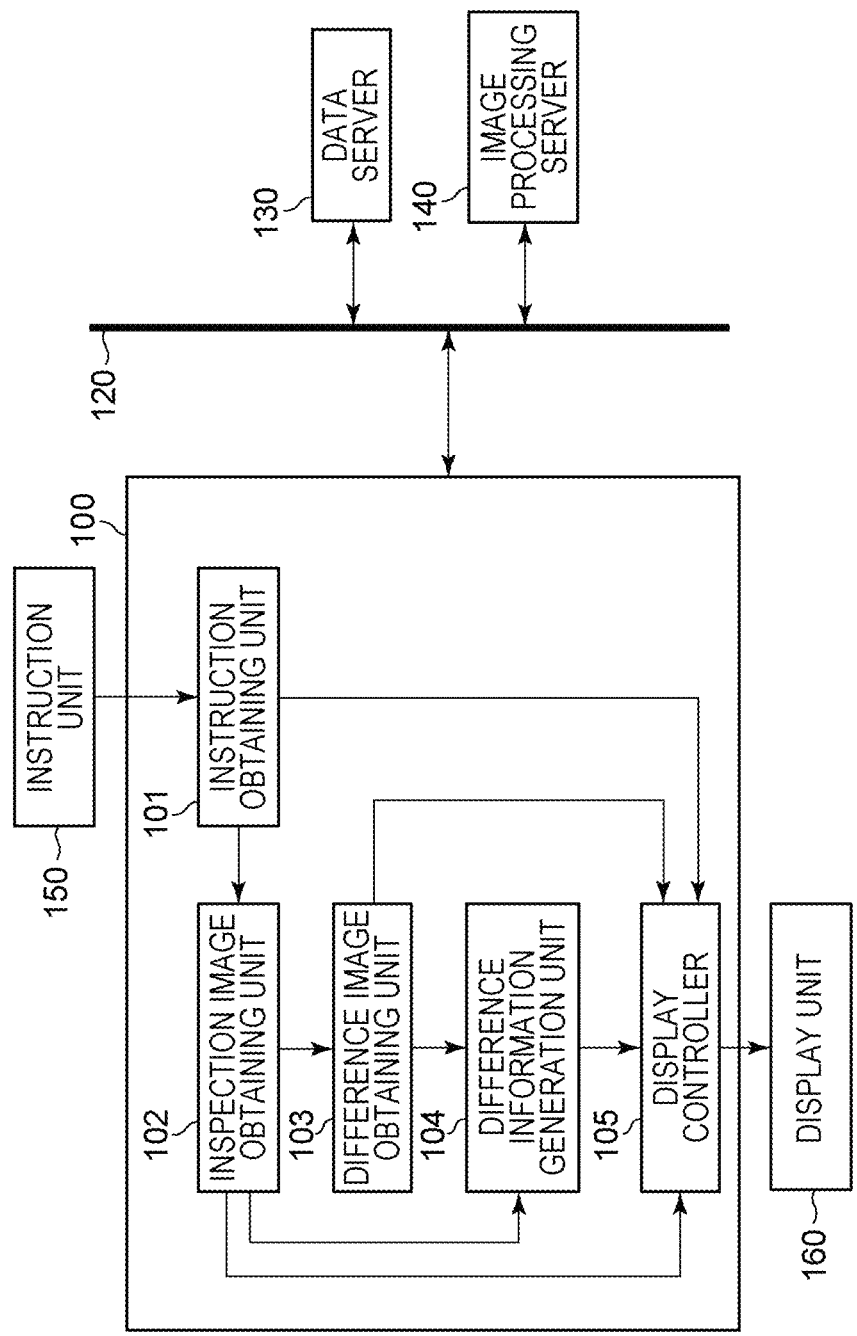

[Fig. 2]
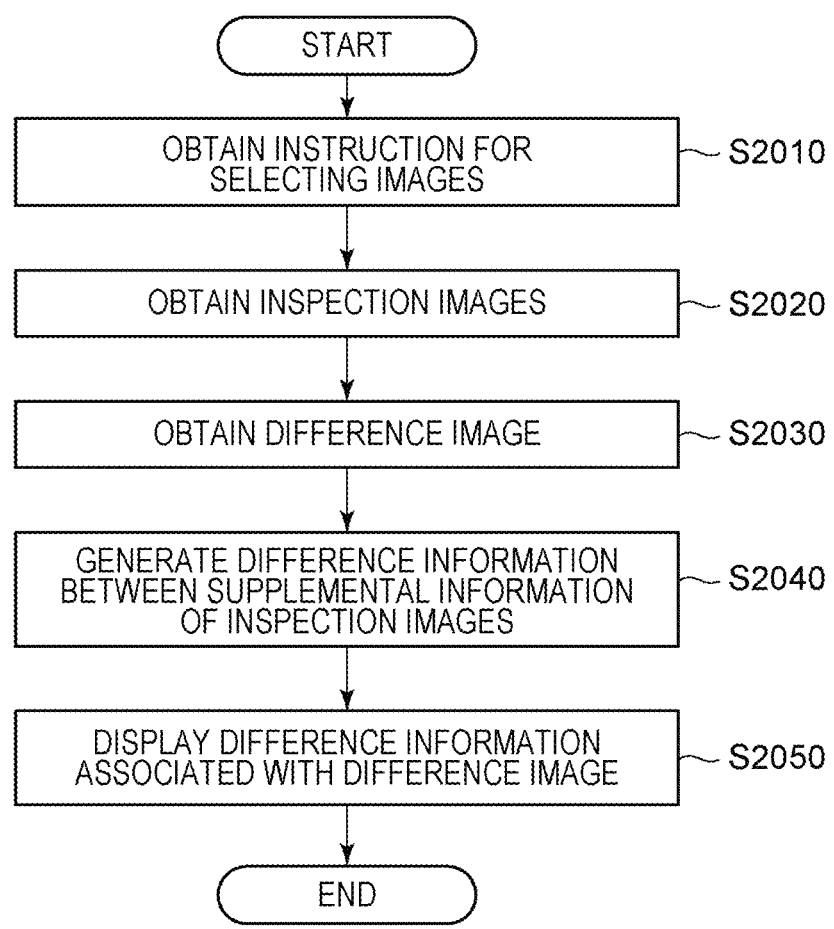

[Fig. 3]
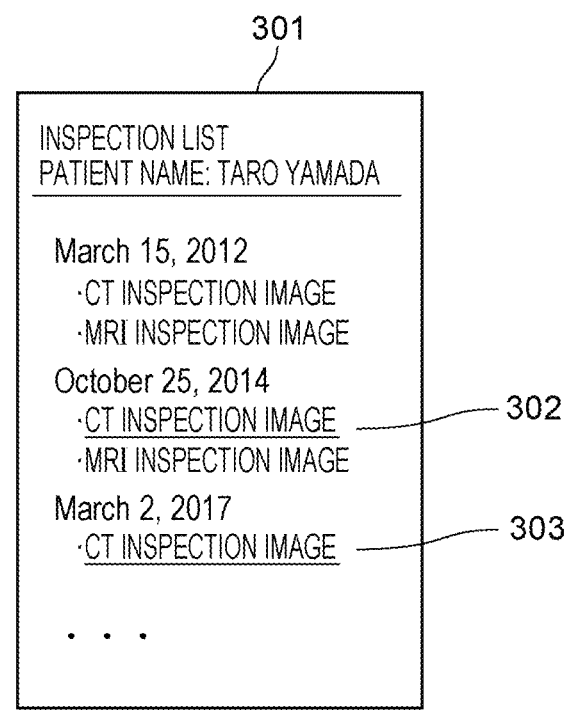

[Fig. 4]

| PROPERTIES OF SUPPLEMENTAL INFORMATION | EXPRESSION FORM OF DIFFERENCE INFORMATION | ITEM NAME |
|---|---|---|
| COMPARISON IN NUMERICAL VALUE IS MEANINGLESS | BINARY (SAME OR DIFFERENT) | PATIENT ID, PATIENT NAME, INSPECTION ID, SERIES ID, RECONFIGURATION FUNCTION OF IMAGING, IMAGING SEQUENCE, IMAGING STATE, INSPECTION BODY POSITION, INSPECTION PORTION, MODALITY, MANUFACTURER, MODEL NAME, AND INSPECTION ORGANIZATION |
| COMPARISON IN NUMERICAL VALUE IS MEANINGFUL | DIFFERENCE BETWEEN VALUES | INSPECTION DATE, INSPECTION TIME, IMAGING DATE, AND IMAGING TIME |
| | MATCHING DEGREE BETWEEN VALUES | SLICE THICKNESS, PIXEL SIZE, PIXEL INTERVAL, THE NUMBER OF SLICES, IMAGE SIZE, AND PATIENT AGE |

[Fig. 6]
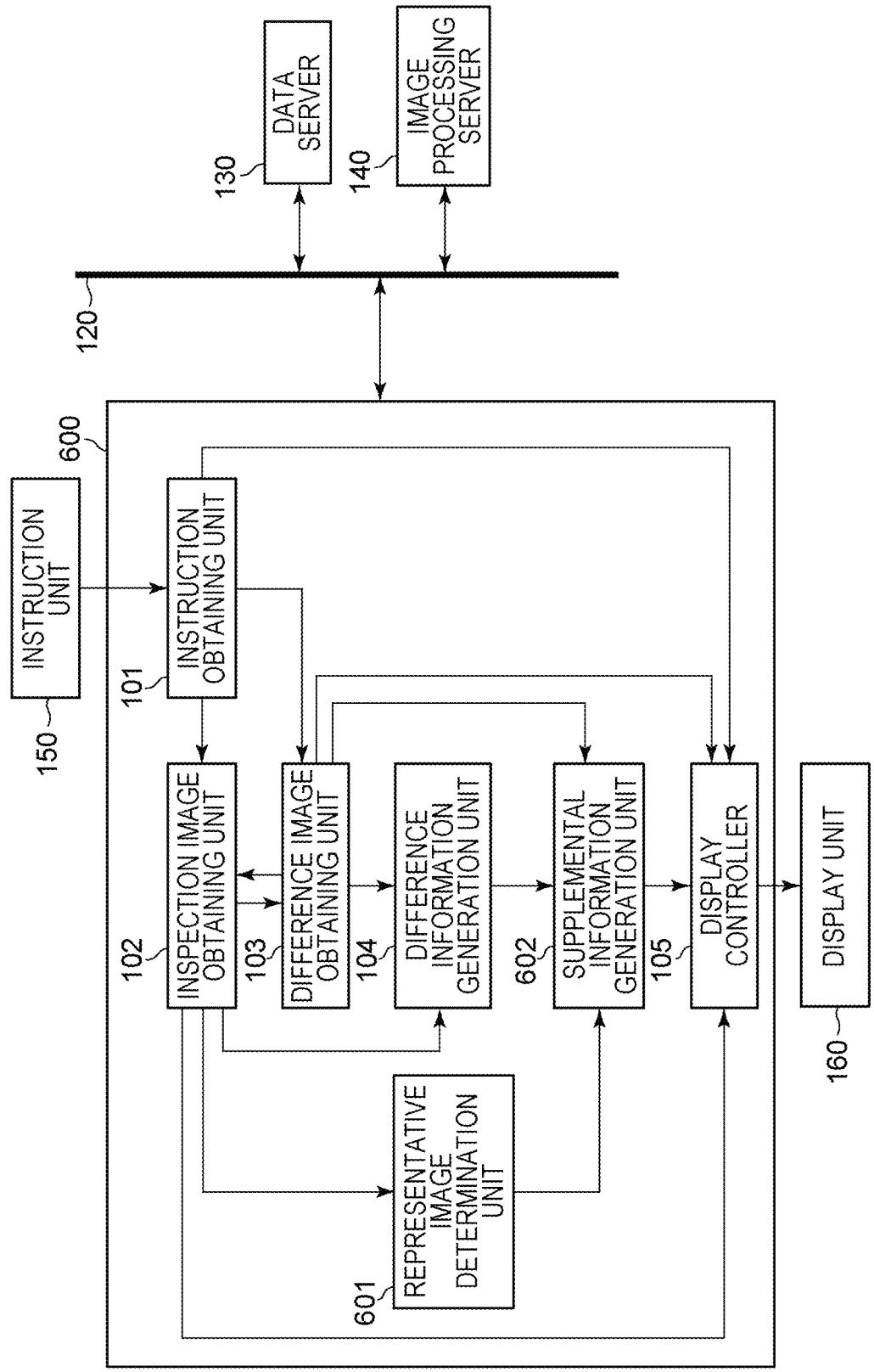

[Fig. 7]
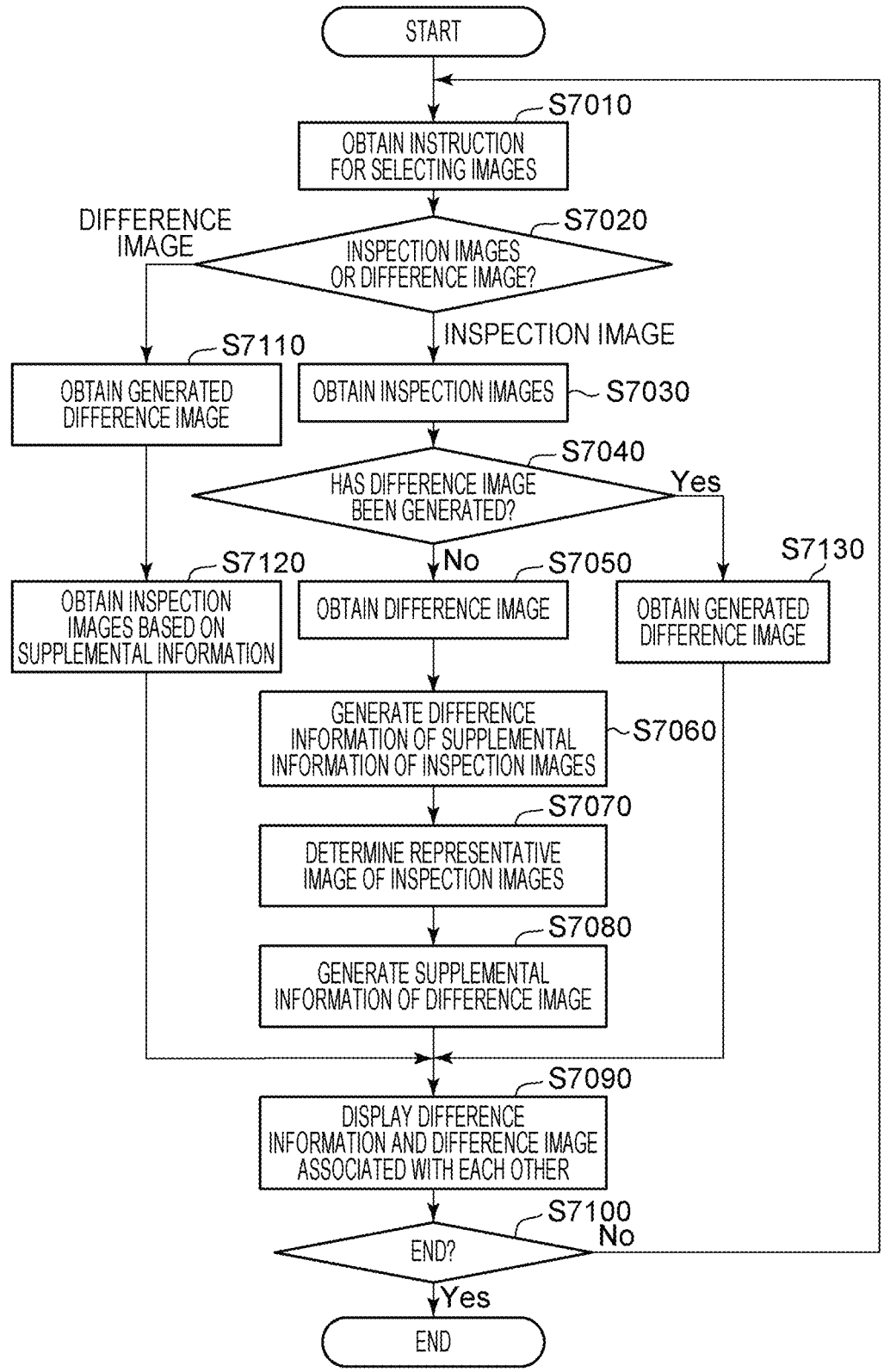

[Fig. 8]
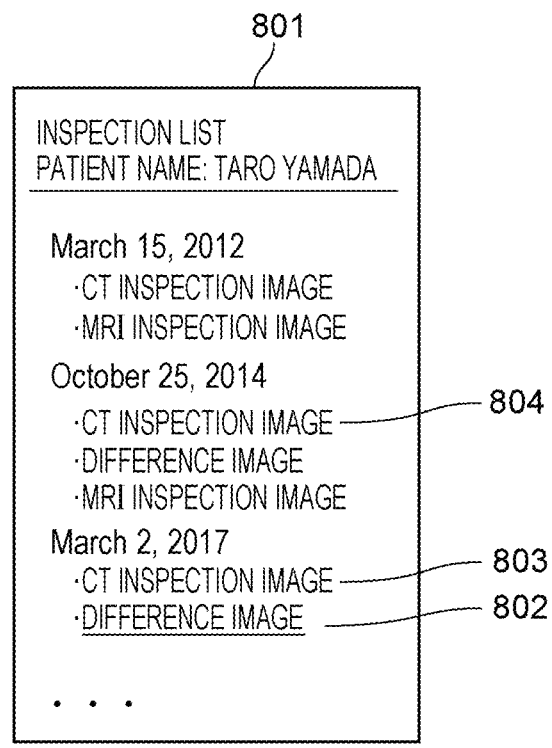

[Fig. 9]

| ITEM NAME | BASIC INFORMATION (STANDARD TAG) 901 | BASE IMAGE INFORMATION (PRIVATE TAG) 902 | COMPARATIVE IMAGE INFORMATION (PRIVATE TAG) 903 | DIFFERENCE INFORMATION (PRIVATE TAG) 904 |
|---|---|---|---|---|
| PATIENT ID | REPRESENTATIVE IMAGE | BASE IMAGE | COMPARATIVE IMAGE | BINARY (SAME/DIFFERENT) |
| PATIENT NAME | REPRESENTATIVE IMAGE | BASE IMAGE | COMPARATIVE IMAGE | BINARY (SAME/DIFFERENT) |
| INSPECTION ID | REPRESENTATIVE IMAGE | BASE IMAGE | COMPARATIVE IMAGE | BINARY (SAME/DIFFERENT) |
| SERIES ID | DIFFERENCE IMAGE (NEW ID) | BASE IMAGE | COMPARATIVE IMAGE | BINARY (SAME/DIFFERENT) |
| INSPECTION DATE | REPRESENTATIVE IMAGE | BASE IMAGE | COMPARATIVE IMAGE | DIFFERENCE BETWEEN VALUES (REFERENCE – COMPARATIVE) |
| IMAGING DATE | REPRESENTATIVE IMAGE | BASE IMAGE | COMPARATIVE IMAGE | DIFFERENCE BETWEEN VALUES (REFERENCE – COMPARATIVE) |
| MODALITY | REPRESENTATIVE IMAGE | BASE IMAGE | COMPARATIVE IMAGE | BINARY (SAME/DIFFERENT) |
| APPARATUS MANUFACTURER | REPRESENTATIVE IMAGE | BASE IMAGE | COMPARATIVE IMAGE | BINARY (SAME/DIFFERENT) |
| INSPECTION PORTION (IMAGE GENERATION PORTION) | DIFFERENCE IMAGE (COMMON REGION) | BASE IMAGE | COMPARATIVE IMAGE | DIFFERENCE BETWEEN VALUES |
| RECONFIGURATION FUNCTION | – | BASE IMAGE | COMPARATIVE IMAGE | BINARY (SAME/DIFFERENT) |
| THE NUMBER OF SLICES | DIFFERENCE IMAGE | BASE IMAGE | COMPARATIVE IMAGE | MATCHING DEGREE OF VALUES |
| SLICE THICKNESS [mm] | DIFFERENCE IMAGE | BASE IMAGE | COMPARATIVE IMAGE | MATCHING DEGREE OF VALUES |
| IMAGE SIZE (HORIZONTAL WIDTH) | DIFFERENCE IMAGE | BASE IMAGE | COMPARATIVE IMAGE | MATCHING DEGREE OF VALUES |
| IMAGE SIZE (VERTICAL WIDTH) | DIFFERENCE IMAGE | BASE IMAGE | COMPARATIVE IMAGE | MATCHING DEGREE OF VALUES |
| PIXEL INTERVAL [mm] | DIFFERENCE IMAGE | BASE IMAGE | COMPARATIVE IMAGE | MATCHING DEGREE OF VALUES |

[Fig. 10]

| ITEM NAME | BASIC INFORMATION (STANDARD TAG) 1001 | BASE IMAGE INFORMATION (PRIVATE TAG) 1002 | COMPARATIVE IMAGE INFORMATION (PRIVATE TAG) 1003 | DIFFERENCE INFORMATION (PRIVATE TAG) 1004 |
|---|---|---|---|---|
| PATIENT ID | "0123" | "0123" | "0123" | "SAME" |
| PATIENT NAME | "TARO YAMADA" | "TARO YAMADA" | "TARO YAMADA" | "SAME" |
| INSPECTION ID | "0002" | "0002" | "0001" | "DIFFERENT" |
| SERIES ID | "0030" | "0020" | "0010" | "DIFFERENT" |
| INSPECTION DATE | "MARCH 2, 2017" | "MARCH 2, 2017" | "OCTOBER 25, 2014" | "2 YEARS 4 MONTHS AND 5 DAYS" |
| IMAGING DATE | "MARCH 2, 2017" | "MARCH 2, 2017" | "OCTOBER 25, 2014" | "2 YEARS 4 MONTHS AND 5 DAYS" |
| MODALITY | "CT" | "CT" | "CT" | "SAME" |
| APPARATUS MANUFACTURER | "B COMPANY" | "B COMPANY" | "A COMPANY" | "DIFFERENT" |
| INSPECTION PORTION (IMAGE GENERATION PORTION) | "CHEST" | "TRUNK" | "CHEST" | "DIFFERENT" |
| RECONFIGURATION FUNCTION | – | "yyy" | "xxx" | "DIFFERENT" |
| THE NUMBER OF SLICES | "306" | "306" | "65" | "21%" |
| SLICE THICKNESS [mm] | "1" | "1" | "5" | "20%" |
| IMAGE SIZE (HORIZONTAL WIDTH) | "512" | "512" | "512" | "SAME (100%)" |
| IMAGE SIZE (VERTICAL WIDTH) | "512" | "512" | "512" | "SAME (100%)" |
| PIXEL INTERVAL [mm] | "0.75×0.75" | "0.75×0.75" | "0.70×0.70" | "93%" |

[Fig. 11]
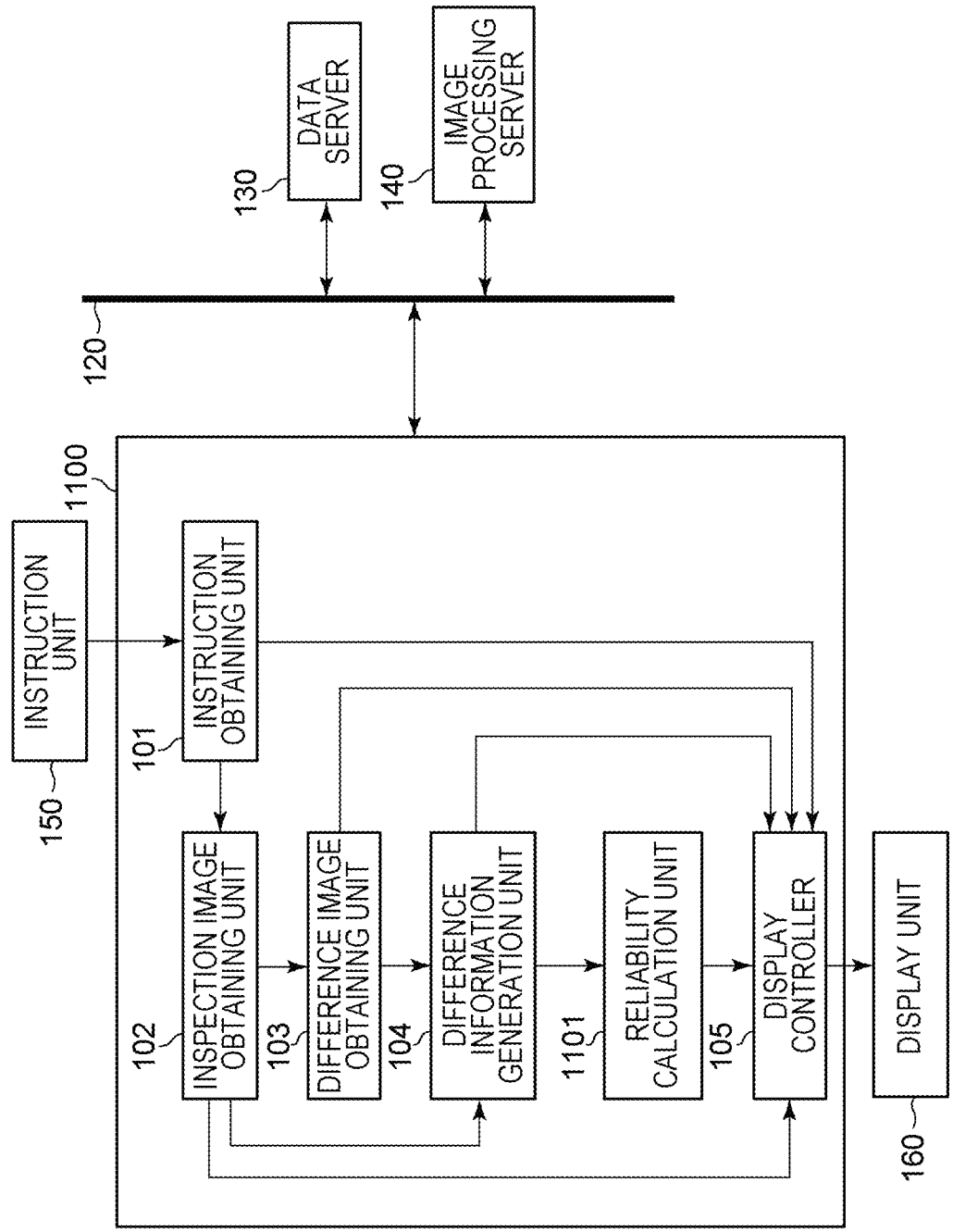

[Fig. 12]
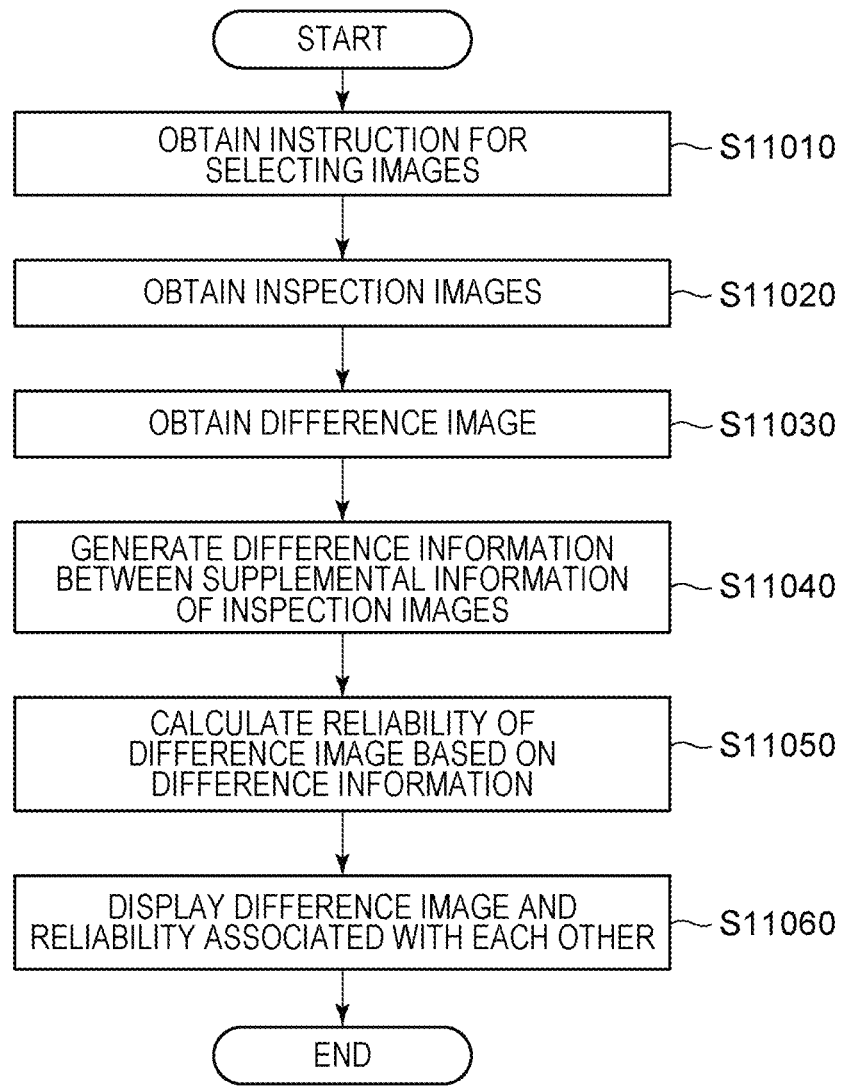

[Fig. 13]
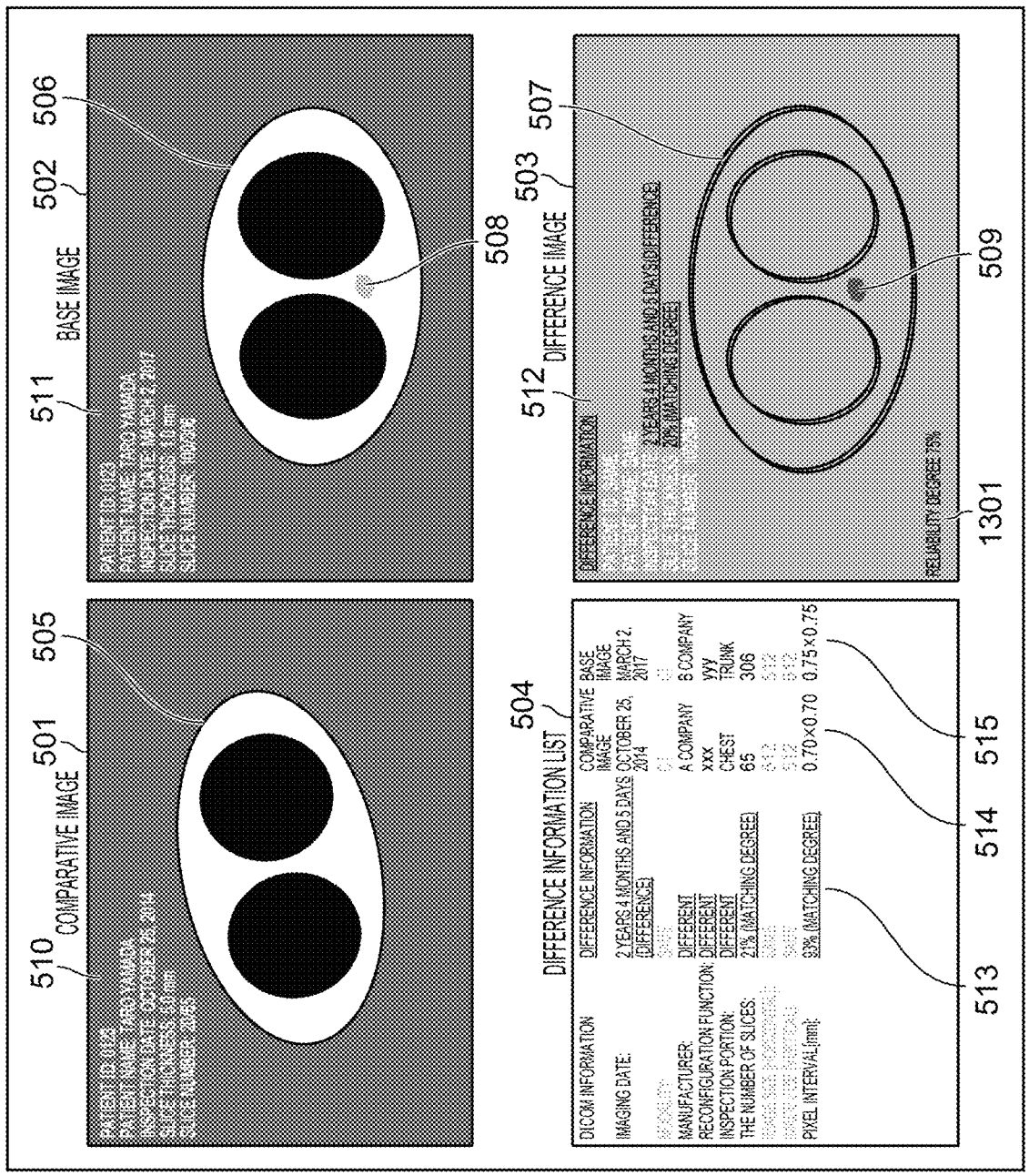

INFORMATION PROCESSING APPARATUS AND METHOD FOR CONTROLLING THE SAME TO GENERATE A DIFFERENCE IMAGE FROM FIRST AND SECOND INSPECTION IMAGES

CROSS-REFERENCE TO RELATED APPLICATIONS

This application is a National Phase application of International Application No. PCT/JP2018/019538, filed May 21, 2018, which claims the benefit of Japanese Patent Application No. 2017-108241, filed May 31, 2017. The disclosures of the above-named applications and patent are hereby incorporated by reference herein in their entirety.

TECHNICAL FIELD

The present invention relates to an information processing apparatus and a method for controlling the information processing apparatus.

BACKGROUND ART

In a medical field, doctors use medical images obtained by various modalities including a magnetic resonance imaging (MRI) apparatus, an X-ray computed tomography (X-ray CT) apparatus, and an ultrasound imaging (US) apparatus for diagnosis. In particular, such a doctor compares a plurality of images captured in different time points with one another for a follow-up of a state of a test object so as to observe a temporal change of the test object. PTL 1 discloses a technique of visualizing a change of a test object by displaying a difference image obtained by calculating differences between pixel values of corresponding pixels in two inspection images being compared.

However, the technique in PTL 1 has a problem in that it is difficult for a user, that is, a doctor, to appropriately evaluate the difference image since the generated difference image is simply displayed.

CITATION LIST

Patent Literature

PTL 1: Japanese Patent Laid-Open No. 2013-126575

SUMMARY OF INVENTION

Solution to Problem

The present invention provides assistance of appropriate evaluation of a difference image performed by a user. The present invention also provides, in addition to such assistance, attainment of function effects which are derived from configurations disclosed in embodiments of the present invention described below but which are not obtained by the general techniques.

According to an embodiment of the present invention, an information processing apparatus includes an image obtaining unit configured to obtain a first inspection image having first supplemental information and a second inspection image having second supplemental information, a difference image obtaining unit configured to obtain a difference image generated using the first and second inspection images, a difference information obtaining unit configured to obtain difference information on a difference between the first supplemental information and the second supplemental information, and an association unit configured to associate the difference information with the difference image.

Further features of the present invention will become apparent from the following description of exemplary embodiments with reference to the attached drawings.

BRIEF DESCRIPTION OF DRAWINGS

FIG. 1 is a diagram illustrating a configuration of an apparatus included in an information processing system according to a first embodiment.

FIG. 2 is a flowchart of an entire processing procedure according to the first embodiment.

FIG. 3 is a diagram illustrating an example of display for a selection of inspection images in an inspection list.

FIG. 4 is a diagram illustrating an example of an expression form of difference information in accordance with properties of supplemental information.

FIG. 5 is a diagram illustrating an example of display of the difference information associated with a difference image.

FIG. 6 is a diagram illustrating a configuration of an apparatus included in an information processing system according to a second embodiment.

FIG. 7 is a flowchart of an entire processing procedure according to the second embodiment.

FIG. 8 is a diagram illustrating an example of display for a selection of a difference image in an inspection list.

FIG. 9 is a diagram illustrating examples of items of supplemental information of the difference image and attributes of contents of descriptions.

FIG. 10 is a diagram illustrating examples of items of the supplemental information of the difference image and detailed contents of descriptions.

FIG. 11 is a diagram illustrating a configuration of an apparatus included in an information processing system according to a third embodiment.

FIG. 12 is a flowchart of an entire processing procedure according to the third embodiment.

FIG. 13 is a diagram illustrating an example of display of a degree of reliability associated with a difference image.

DESCRIPTION OF EMBODIMENTS

Hereinafter, preferred embodiments of an information processing apparatus and a method for controlling the information processing apparatus will be described in detail with reference to the accompanying drawings. Note that the scope of the invention is not limited to examples illustrated in the drawings.

First Embodiment

An information processing apparatus according to this embodiment displays, in addition to a difference image of two inspection images, supplemental information associated with the difference image. Specifically, the information processing apparatus according to this embodiment is mainly characterized by generating difference information associated with a difference between supplemental information of two inspection images and displaying the difference information associated with a difference image of the inspection images. The information processing apparatus displays a difference between supplemental information for a user in addition to a difference between the two inspection images so that the user may more appropriately evaluate a difference image. A configuration and a process of this embodiment will now be described with reference to FIGS. 1 to 4.

FIG. 1 is a diagram illustrating a configuration of an information processing system according to this embodiment. As illustrated in FIG. 1, an information processing apparatus 100 according to this embodiment is connected to a data server 130 and an image processing server 140 through a network 120.

The data server 130 has a plurality of inspection images. The data server 130 has first and second inspection images which are three-dimensional tomographic images. The first and second inspection images are obtained by capturing a test object under different conditions (different modalities, different imaging modes, different date and times, different body positions, or the like) in advance. Examples of the modalities which capture such a three-dimensional tomographic image include an MRI apparatus, an X-ray CT apparatus, a three-dimensional ultrasound imaging apparatus, a photoacoustic tomography apparatus, positron emission tomography/single photon emission CT (PET/SPECT), and an optical coherence tomography (OCT) apparatus. The first and second inspection images may be any type of image as long as a difference image is generated using the first and second inspection images. The first and second inspection images may be simultaneously captured by different modalities or in different imaging modes, for example. Furthermore, the first and second inspection images may be obtained by capturing the same patient by the same modality in the same body position in different date and times for a follow-up.

Note that each of the first and second inspection images is a three-dimensional image configured as an aggregate (a tomographic image group) of two-dimensional tomographic images (slice images). A position and an orientation of each of the two-dimensional tomographic images constituting the three-dimensional image are converted into a reference coordinate system (a coordinate system in a space based on the test object) before being stored in the data server 130. The first and second inspection images are input to the information processing apparatus 100 in response to an instruction issued by a user operating an instruction unit 150. Note that the inspection images are not limited to three-dimensional tomographic images and may be two-dimensional images, such as simple X-ray images or normal cameral images.

Here, information held by each of the inspection images will be described. Each of the inspection images has supplemental information in addition to image data constituted by pixel values. The supplemental information indicates various information associated with the corresponding inspection image. The supplemental information includes information on a patient ID, a patient name, an inspection ID, an inspection date (a day when the inspection image is obtained), identification information of a group of tomographic images (a series ID), a date of imaging, a modality, and a manufacturer, for example. The supplemental information further includes information on a reconfiguration function of imaging, an inspection portion, the number of two-dimensional tomographic images constituting the inspection image (the number of slices), a thickness of the slices (a slice thickness), an image size, and a pixel interval, for example. Specifically, the supplemental information includes at least one item.

The supplemental information of this embodiment is recorded in the inspection image as header information of the inspection image. The supplemental information may be stored as header information based on the Digital Imaging and Communication in Medicine (DICOM) which is a general standard of supplemental information of medical images, for example. Note that the supplemental information is not limited to the information described above and may be any information as long as the information is associated with the inspection image. Furthermore, since the supplemental information is associated with the inspection information, when data on the inspection image is input or output, the supplemental information is also input or output in a state in which the supplemental information is included in the inspection image along with the image data. Alternatively, the supplemental information may be stored in a file or a database separately from the inspection image. In this case, the information processing apparatus 100 accesses the file or the database where appropriate to refer to the supplemental information.

The image processing server 140 is installed in a hospital or a cloud as a server. The image processing server 140 performs image processing in response to a received processing request. Specifically, the image processing server 140 receives the first and second inspection images to be subjected to a difference image generation process from the information processing apparatus 100 when receiving a request for generating a difference image from the information processing apparatus 100. Note that the image processing server 140 may directly receive the first and second inspection images from the data server 130. When receiving the first and second inspection images, the image processing server 140 performs a positioning process so that the first and second inspection images coincide with each other (so that pixels in the same portion of the test object are associated with each other). Then the image processing server 140 generates a difference image by calculating differences between pixel values of the images after the positioning and outputs the difference image to the information processing apparatus 100.

Note that the second inspection image serves as a base of the positioning, and therefore, is referred to as a base image (or a reference image). On the other hand, the first inspection image is to be subjected to geometric transform with reference to the second inspection image, and therefore, is referred to as a comparative image (a floating image).

The information processing apparatus 100 performs information processing when receiving a processing request from the user operating the instruction unit 150 and outputs a result of the processing to a display unit 160. The information processing apparatus 100 functions as a terminal apparatus for interpretation of radiogram to be operated by the user, such as a doctor. The information processing apparatus 100 performs transmission of data to and reception of data from the data server 130 and the image processing server 140 and requests performance of processing.

The operations of the information processing apparatus 100 will now be described in detail. The information processing apparatus 100 transmits the first and second inspection images (a past image of a test object captured at a time of past inspection and a current image of the same test object captured at a time of inspection after the past image is captured) obtained from the data server 130 to the image processing server 140 as targets of the generation of a difference image. The information processing apparatus 100 receives the generated difference image from the image processing server 140. The information processing apparatus 100 displays the latest difference image in the display unit 160 along with the first and second inspection images.

The information processing apparatus 100 includes the following components. An instruction obtaining unit 101 obtains an instruction issued by the user operating the instruction unit 150. An inspection image obtaining unit 102 obtains information on the first and second inspection images input to the information processing apparatus 100. A difference image obtaining unit 103 obtains a difference image generated using the first and second inspection images by the image processing server 140. A difference information generation unit 104 generates difference information indicating a difference between the supplemental information of the first and second inspection information. A display controller 105 performs control of output of information on the obtained difference image or the like to the display unit 160.

The instruction unit 150 includes arbitrary devices, such as a mouse and a keyboard. Specifically, the instruction unit 150 functions as a device which transmits an instruction issued by the user to the information processing apparatus 100. That is, the instruction unit 150 transmits a signal associated with a click of the mouse or a press of the keyboard performed by the user to the instruction obtaining unit 101.

The display unit 160 is constituted by an arbitrary devices, such as a liquid crystal device (LCD) or a cathode ray tube (CRT). The display unit 160 displays images, supplemental information, and the like for interpretation of radiogram performed by the doctor. Specifically, the display unit 160 displays tomographic images extracted from the first and second inspection images and the difference image obtained from the information processing apparatus 100. The display unit 160 further displays a graphic user interface (GUI) used to obtain an instruction issued by the user, such as a doctor. The user may freely perform switching from one of the tomographic images of the first inspection image, the second inspection image, or the difference image being displayed to one of the others of the tomographic images which is arranged in a depth direction of the tomographic images using the GUI. The display unit 160 further displays a GUI used by the user, such as a doctor, to select inspection images in an inspection list of a patient.

Note that, in the information processing system according to this embodiment, the information processing apparatus 100 and the image processing server 140 are installed physically separated positions and connected to each other through the network 120. However, the installation of the apparatuses is not limited to this. The information processing apparatus 100 and the image processing server 140 may be integrally configured as a single apparatus, for example. In this case, input/output of data through the network 120 between the information processing apparatus 100 and the image processing server 140 may be replaced by input/output of data in the single apparatus. Specifically, a process of transmitting the first and second inspection images to be subjected to the image difference process from the information processing apparatus 100 to the image processing server 140 is replaced by data input/output in the single apparatus. Furthermore, a process of receiving the difference image generated by the image processing server 140 performed by the information processing apparatus 100 is replaced by data input/output in the single apparatus.

FIG. 2 is a flowchart of an entire processing procedure executed by the information processing apparatus 100.

S2010: Obtainment of Instruction for Image Selection

In step S2010, the instruction obtaining unit 101 obtains an instruction for selecting images issued by the user from the instruction unit 150. Specifically, the instruction obtaining unit 101 obtains an instruction for selecting the first inspection image (the comparative image) and the second inspection image (the base image) which are sources of the difference image in the inspection list displayed by the display unit 160 issued by the user. The instruction obtaining unit 101 outputs information on the instruction for image selection to the inspection image obtaining unit 102.

FIG. 3 is a diagram illustrating an example of display for a selection of the inspection images in the inspection list. An inspection list 301 includes inspection images obtained by inspection performed a plurality of times on a specific patient. In this embodiment, the user selects one of items of the list displayed in the display unit 160 (for example, "CT inspection image" in Inspection Date: Oct. 25, 2014) by a mouse click or the like so as to select an inspection image corresponding to the item.

It is assumed that the user selects two inspection images (the first and second inspection images) 302 and 303 in the inspection list 301 in FIG. 3. Here, the first inspection image 302 indicates a past image obtained by CT inspection (Inspection Date: Oct. 25, 2014), and the second inspection image 303 indicates a current image obtained by the CT inspection (Inspection Date: Mar. 2, 2017). Character strings indicating the inspection images 302 and 303 are emphasized so that selection of the images is easily recognized. Note that, according to this embodiment, one of the two inspection images selected by the user which corresponds to a latest imaging date and time (the current image) is determined as the second inspection image (the base image) and the other of the two inspection images which corresponds to an older imaging date and time (the past image) is determined as the first inspection image (the comparative image). Alternatively, one of the inspection images which is selected first by the user may be determined as the second inspection image (the base image) and the other one which is selected second may be determined as the first inspection image (the comparative image). Furthermore, the user may directly specify the base image and the comparative image.

S2020: Obtainment of Inspection Images

In step S2020, the inspection image obtaining unit 102 obtains the first and second inspection images from the data server 130 in response to an instruction for selecting inspection images obtained by the instruction obtaining unit 101. The inspection image obtaining unit 102 outputs the obtained first and second inspection images to the difference image obtaining unit 103, the difference information generation unit 104, and the display controller 105. Specifically, the process in step S2020 corresponds to an example of an image obtaining unit which obtains the first inspection image having first supplemental information and the second inspection image having second supplemental information.

S2030: Obtainment of Difference Image

In step S2030, the difference image obtaining unit 103 outputs the first and second inspection images to the image processing server 140 and requests the image processing server 140 to generate a difference image. The difference image obtaining unit 103 obtains a difference image generated by the image processing server 140 using the first and second inspection images. The difference image obtaining unit 103 outputs the obtained difference image to the difference information generation unit 104 and the display controller 105. Specifically, the process in step S2030 corresponds to an example of a difference image obtaining unit which obtains the difference image generated using the first and second inspection images.

In the case where the information processing apparatus 100 and the image processing server 140 are integrally configured as a single apparatus as described above, the difference image obtaining unit 103 performs the generation of a difference image instead of the image processing server 140. Specifically, the difference image obtaining unit 103 performs a positioning process so that the first inspection image matches the second inspection image and generates a difference image by calculating differences between pixel values of both of the images after the positioning. Here, any one of general positioning methods may be used. Note that the process of positioning images may not be required if the same portion of the object in the first and second inspection images is seen to be positioned in the same coordinate. Furthermore, the difference image may be generated using three or more inspection images.

S2040: Generation of Information on Difference Between Supplemental Information of Inspection Images In step S2040, the difference information generation unit 104 generates difference information indicating a difference between supplemental information of the first and second inspection images. Here, the difference information includes information on results of differences between the same items included in the supplemental information of the first and second inspection images. The difference information generation unit 104 outputs the generated difference information to the display controller 105. Specifically, the process in step S2040 corresponds to an example of a difference information obtaining unit which obtains difference information associated with a difference between the first supplemental information and the second supplemental information. Hereinafter, content and a calculation method of the difference information will be described in detail.

FIG. 4 is a diagram illustrating an example of an expression form of the difference information in accordance with properties of supplemental information. The supplemental information mainly includes two types of item, that is, an item which is meaningless in a comparison by numerical values, such as a name or a type, and an item which is meaningful in a comparison by numerical values (a comparison between distances or a comparison between magnitudes), such as a date and time or a size.

Difference information of the item which is meaningless in a comparison by numerical values may not be represented by a numerical value. Therefore, the information processing apparatus 100 represents such an item by a binary indicating whether values of the item are the same (a state in which "the values are the same" is also included in the difference information). Examples of the item which is meaningless in a comparison by numerical values include items 401 in FIG. 4. Specifically, the items include a patient ID, a patient name, an inspection ID, a series ID, a reconfiguration function of imaging, an imaging sequence, an imaging state, an inspection body position, an inspection portion, a modality, a manufacturer, a model name, and an inspection organization. In a case where a patient ID of the supplemental information of the first inspection image and a patient ID of the supplemental information of the second inspection image are the same as each other ("0123" for the first inspection image and "0123" for the second inspection image, for example), the difference information is indicated by "Same". On the other hand, the patient IDs are different from each other ("0123" for the first inspection image and "2345" for the second inspection image, for example), the difference information is indicated by "Different".

On the other hand, the information processing apparatus 100 represents difference information of the item which is meaningful in a comparison by numerical values by a numerical value. In this case, the difference information includes two types of item, that is, an item which is meaningful in an absolute difference and an item which is meaningful in a relative difference. Examples of the item which is meaningful in an absolute difference include items 402, such as an inspection date, an inspection time, an imaging date, and an imaging time. For example, an item representing a date and time, such as the inspection date, is meaningful in an absolute difference of a time on a numerical value axis. For example, the user may recognize a degree of a time interval between two inspection images with reference to a difference between inspection dates (obtainment dates). Furthermore, the user may recognize whether a difference value visualized in a difference image is generated within a short period ("3 months", for example) or a long period ("5 years", for example). In this way, as for the item which is meaningful in an absolute difference, the information processing apparatus 100 employs a difference between values of the supplemental information as it is as the difference information.

On the other hand, examples of the item which is meaningful in a relative difference include items 403, such as a slice thickness, a pixel size, a pixel interval, the number of slices, an image size, and a patient age. For example, a difference between absolute values of slice thicknesses is useless. Specifically, in a case where slice thicknesses of the first and second inspection images are "1 mm" and "2 mm", respectively, a difference between the values is "1 mm". However, the difference between the slice thicknesses of "1 mm" does not indicate whether the difference is large for the two original inspection images. In a case where the slice thicknesses of the first and second inspection images are "1 mm" and "2 mm", respectively, for example, the difference of "1 mm" between the thicknesses accounts for large proportions of the original slice thicknesses of the inspection images (proportions of the difference are 1.0 time and 2.0 times, respectively). However, in a case where the slice thicknesses of the first and second inspection images are "4 mm" and "5 mm", respectively, for example, the difference of "1 mm" between the thicknesses does not account for large proportions of the original slice thicknesses of the inspection images (proportions of the difference are 0.25 times and 0.2 times, respectively). As for such an item, a relative difference between the inspection images, that is, a degree of relative matching, is importantly obtained.

Therefore, in this embodiment, a matching degree of values of the supplemental information is employed as the difference information of the supplemental information in such an item which is meaningful in a relative difference. Specifically, the following expression is employed as a matching degree M.

$$M = \text{(Smaller Value)} / \text{(Larger Value)} \quad (1)$$

It is assumed that the examples of the slice thicknesses are employed in Expression (1). When the slice thicknesses are "1 mm" and "2 mm", a matching degree M is 50% ("1 mm"/"2 mm"=0.50). When the slice thicknesses are "4 mm" and "5 mm", a matching degree M is 80% ("4 mm"/"5 mm"=0.80). According to the matching degree M, the user may relatively recognize a degree of matching. Specifically, the user may relatively recognize a degree of a difference (a large difference of 50% in the former case and a small difference of 20% in the latter case). As other examples, a matching degree between the numbers of slices, a matching degree between image sizes, and a matching degree between pixel intervals may be obtained by the same calculation using Expression (1). Note that the method for calculating the matching degree M is not limited to Expression (1), and any calculation method may be employed as long as a relative matching degree between two values may be quantized. A value obtained by dividing "an absolute value of a difference between two values" by "a mean value between the two values" may be used as the matching degree M.

Note that the inspection portion is an example of the item which is meaningless in a comparison by numerical values in FIG. 4. This is because the item is represented by a term indicating a portion of a body, such as "CHEST" or "HEAD". However, a matching degree between inspection portions may be calculated as follows. Specifically, in step S2030, the image processing server 140 performs positioning on the first and second inspection images and generates a difference image by calculating differences between pixel values in a common region. That is, the image processing server 140 may obtain the common region (the difference image) and an uncommon region (other region) using the first and second inspection images.

Therefore, the following expression is employed to obtain a matching degree between inspection portions of the first and second inspection images.

$$M = (\text{region 1} \cap \text{region 2})/(\text{region 1} \cup \text{region 2}) \quad (2)$$

In Expression (2), "region 1" and "region 2" indicate three-dimensional image regions of the first and second inspection images, respectively. Expression (2) indicates a Jaccard index which is a method for obtaining a matching degree between region 1 and region 2. Here, "(region 1 ∩ region 2)" in Expression (2) indicates the common region (the difference image) of the inspection images and is obtained in advance. Accordingly, information on (region 1 ∪ region 2)

may be calculated using information on region 1, information on region 2, and information on "(region 1 ∩ region 2)", and therefore, Expression (2) may be solved. Note that any general method, such as a Dice coefficient or a Simpson coefficient, may be employed as the matching degree M as long as a matching degree between region 1 and region 2 is obtained.

Although the matching degree M between values of the supplemental information is employed as the difference information between the supplemental information in the foregoing description, a mismatching degree between the values of the supplemental information may be employed. A mismatching degree M' may be calculated as follows: M'=1−M. By this, the user may more directly recognize a relative difference between the supplemental information when compared with the matching degree M.

Note that the difference information generation unit 104 calculates difference information in the items 401 to 403 of the supplemental information illustrated in FIG. 4. However, the supplemental information used to obtain the difference information is not limited to this, and any information may be employed as long as the information is associated with the inspection images. Furthermore, instead of the calculation of the difference information on all the items of the supplemental information, only a specific number of the items of the supplemental information may be subjected to the calculation of difference information. For example, items which affect quality of a difference image may be specified in advance and only difference information of the specified items may be calculated.

Furthermore, items to be specified which are to be subjected to the calculation of difference information may be changed depending on a type of the inspection images, for example. Supplemental information associated with imaging parameters of inspection images is different between a case where a modality which captures the inspection images is the CT and a case where the modality is the MRI. In the case of the CT, supplemental information unique to the CT, such as a reconfiguration function, is used. However, in the case of the MRI, such supplemental information is not used. Therefore, the difference information generation unit 104 generates difference information of the specified item unique to a modality depending on a type of modality with reference to modality information included in the supplemental information of the inspection images. The difference information generation unit 104 generates difference information by the method described above only when the types of modality of the first and second inspection images match each other. The difference information generation unit 104 generates difference information only for general items (an inspection date, a pixel size, a patient age, and the like) which do not rely on the modality when the types of modality do not match each other.

S2050: Display Difference Information Associated with Difference Image

In step S2050, the display controller 105 displays the first and second inspection images obtained from the inspection image obtaining unit 102 in the display unit 160. The display controller 105 further displays the difference information which is obtained from the difference information generation unit 104 and which is associated with the difference image obtained from the difference image obtaining unit 103 in the display unit 160. Specifically, the process in step S2050 corresponds to a display control unit which displays the difference information and the difference image which are associated with each other in a display unit.

Figure 5:
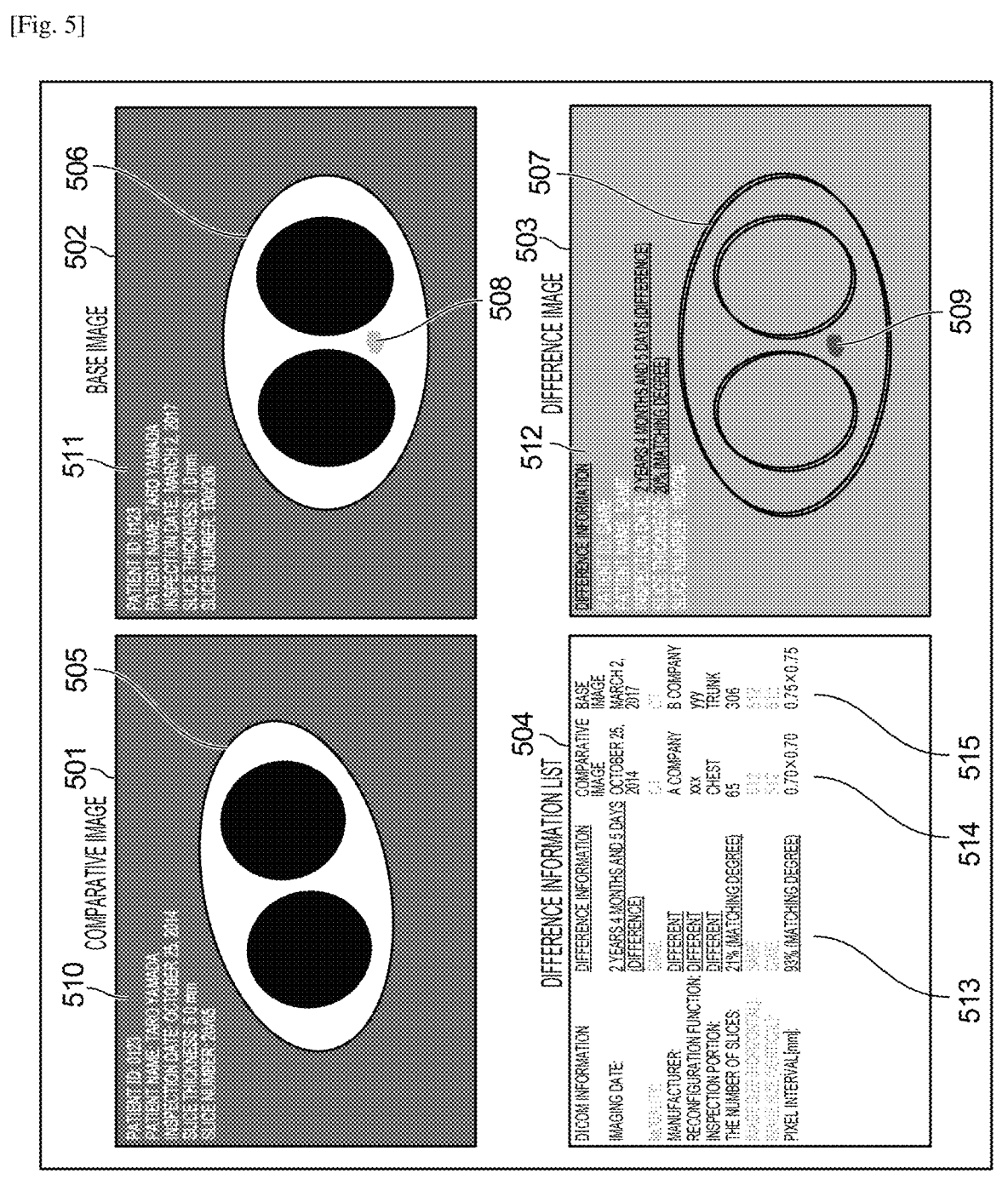

FIG. 5 is a diagram illustrating an example of the display of the difference information associated with the difference image. In FIG. 5, tomographic images 501 and 502 correspond to the first and second inspection images, respectively. In FIG. 5, the first inspection image serves as a comparative image and the second inspection image serves as a base image of the same object. Test objects 505 and 506 are rendered in the tomographic images 501 and 502, respectively. In FIG. 5, the tomographic images 501 and 502 are obtained by slicing a body of the test object in an axial direction. The test objects 505 and 506 correspond to the body of the test object which is displayed in a sliced manner. It is recognized that position and orientations and shapes of the bodies 505 and 506 of the test object in the comparative image and the base image are shifted from each other when the bodies 505 and 506 of the test object are compared with each other.

A lesion 508 is generated in the base image. A tomographic image 507 corresponds to the difference image. A tomographic image 503 represents the difference image (in the same tomographic position) corresponding to the tomographic image 502. The tomographic image 507 is information indicating a difference value on the tomographic image 503 which corresponds to a portion in the vicinity of a contour of the body of the test object on the tomographic image 502. The positional shift is generated as an artifact since a positioning state of the test object between the images is not sufficient. A lesion 509 corresponds to the lesion 508 in the tomographic image 502 and indicates a difference value in the tomographic image 503. The user may easily recognize a lesion generated in temporal change between the base image and the comparative image by checking the lesion 509 in the tomographic image 503 of the difference image. Note that the display of the inspection images and the difference image may be performed by any of general methods instead of the method described above. For example, multi-planar reconstruction (MPR) images or maximum Intensity Projection (MIP) images of the inspection images and the difference image may be displayed. Furthermore, the difference image and the second inspection image may be displayed in a superposed manner.

Sections 510 and 511 indicate portions of the supplemental information of the first and second inspection images (at least a number of the items included in the supplemental information). In the sections 510 and 511, items which are particularly useful when interpretation of radiogram is performed by the user, that is, a doctor, in the entire supplemental information of the inspection images are displayed. The items to be displayed on the inspection images in an overlapping manner may be specified by a setting file stored in advance or specified by displaying a setting screen and accepting a selection, by the user, of items to be displayed. Difference information 512 is displayed in association with the difference image and indicates information on a difference between the supplemental information of the first and second inspection images. The difference information corresponds to the displayed items in the items included in the supplemental information of the first and second inspection images. As described above, since the display controller 105 displays the difference information between the supplemental information such that the difference information is superposed on the difference image, the user may easily recognize difference values in the difference image and the difference information between the supplemental information which are associated with each other. Specifically, the display control corresponds to an example of the display control unit characterized by displaying difference information associated with a difference image on the difference image in the superposed manner.

The difference information may be displayed by pop-up or the difference information may be displayed in a region other than a region including the difference image when a selection of the difference image is detected. In this case, the regions may be associated with each other by a line in the display. The mode in which the difference image and the difference information are displayed in an associated manner is not limited to the display form described in this embodiment. Furthermore, it is preferable that the difference information of the items corresponding to the supplemental information 510 and the supplemental information 511 is displayed as difference information 512 as illustrated in FIG. 5. By this, the difference information between the supplemental information which is particularly useful for the interpretation of radiogram may be recognized while the difference information is associated with difference values of the difference image. Note that items which affect quality of the difference image may be specified in advance as items in which the difference information is displayed in the items of the supplemental information 510 and the supplemental information 511, and only the selected items may be displayed. Furthermore, items in which the difference image is displayed may be specified independently from the display items of the supplemental information of the inspection images.

In this embodiment, different display forms are employed for different types of item, that is, items corresponding to the supplemental information of "Same" and items corresponding to the supplemental information of "Different" in the difference information 512. Specifically, the display control corresponds to an example of the display control unit characterized by differentiating a display form between items having difference and items which do not have difference. The supplemental information of "Same" indicates a case where values of the two supplemental information is the "Same" in a case of items having values of supplemental information which may not be represented by numerical values. On the other hand, the supplemental information of "Same" indicates a case where a matching degree of values of the two supplemental information is "1.0 (100%)" in a case of items having values of supplemental information which may be represented by numerical values. The supplemental information of "Different" indicates a case other than the case of the supplemental information of "Same" described above.

As a method for changing a display form, a method for displaying items corresponding to the supplemental information of "Different" in an emphasized manner when compared with the items corresponding to the supplemental information of "Same" may be employed as illustrated in the difference information 512 of FIG. 5. As another method, a method for only displaying the items corresponding to the supplemental information of "Different" and not displaying the items corresponding to the supplemental information of "Same" may be employed. By this, the user may easily recognize only the items in which a difference is generated in the difference information. In the example of FIG. 5, the user may easily recognize that a difference value of the lesion 509 in the displayed difference image is generated in a period between inspection dates of 2 years 4 months and 5 days with reference to the difference information 512. By this, the user may appropriately recognize a temporal change of the lesion when compared with a case only the difference image is used.

Furthermore, the user may determine quality of the difference image in accordance with a magnitude of the difference of the inspection dates. If the difference between the inspection dates is large, a change of the test object is large in the period, and therefore, a shift between anatomical structures rendered in the inspection images is large. Accordingly, accuracy of positioning between the inspection images having the large shift is degraded, and furthermore, it is highly likely that quality of the difference image is degraded. On the other hand, if the difference between the inspection dates is small, a shift between the anatomical structures is small, and therefore, it is not likely that the quality of the difference image is degraded. Furthermore, the user may determine the difference between the inspection dates using the inspection dates displayed in the tomographic images 501 and 502 which are the comparative image and the base image, respectively. However, a burden thereof may be omitted in this embodiment.

Furthermore, the user may easily recognize that the tomographic image 503 of the displayed difference image is generated using the inspection images having a matching degree of 20% of the slice thicknesses with reference to the difference information 512. Accordingly, the user may recognize that the difference image is generated from inspection images having a large difference between resolutions in a depth direction of the tomographic images. Furthermore, the user may recognize that it is likely that noise caused by image processing performed on the images of the different resolutions is mixed in the difference image, and therefore, the noise may adversely affect the quality of the difference image. Accordingly, a risk in which the user mistakenly determines the noise as a lesion may be reduced.

The description described above correspond to an example of the display control unit characterized by differentiating a display form of the difference information of the items depending on degrees of influence from differences of the items on the difference image.

A difference information list 504 includes difference information as a list. In this embodiment, the difference information list 504 provides information on the items of the supplemental information other than the difference information 512 displayed in the tomographic image 503. Specifically, the display control corresponds to an example of the display control unit characterized by displaying the difference information corresponding to the items which has not been displayed, as a list in the display unit. The display of the difference information list 504 is useful not only for the interruption of radiogram but also recognition by the user of the entire generated difference information. The difference information list 504 may be displayed at all time or displayed only when the user specifies an icon, not illustrated, such as an icon indicating "detailed display of difference information". By this, while display of the difference information list 504 is not specified, a different object may be displayed in the display region instead so that the region is efficiently used. Alternatively, the difference information list 504 may be displayed by a pop-up window or the like.

Note that difference information 513 is included in the difference information list 504 and supplemental information 514 and 515 correspond to the first and second inspection images (the comparative image and the base image, respectively) which are sources of the difference information of the individual items. In this embodiment, as with the case of the difference information 512, different display forms are employed for different types of item, that is, items corresponding to the supplemental information of "Same" and items corresponding to the supplemental information of "Different" in the difference information 513. Furthermore, as for a method for changing the display form, as with the case of the difference information 512, the display controller 105 displays the supplemental information in a state in which the items corresponding to the supplemental information of "Different" are more emphasized compared with the items corresponding to the supplemental information of "Same". Alternatively, the display controller 105 may display only the items corresponding to "Different" and not display the items corresponding to "Same" after determining whether the supplemental information of the individual items corresponds to "Different" or "Same". Specifically, the display control corresponds to an example of the display control unit characterized in that difference information of the items in which a difference is generated is not displayed. By this, the user may easily recognize the number of items in which a difference is generated in the difference information and degrees of the differences of the items. When the number of items in which a difference is generated is large and degrees of the differences are large, differences in various conditions between the two inspection images which are sources of the difference image are large. Accordingly, the user may determine that the quality of the difference image may be degraded. On the other hand, when the number of items in which a difference is generated is small and degrees of the differences are small, differences in various conditions between the two inspection images which are sources of the difference image are small. Accordingly, the user may determine that the quality of the difference image may be high.

The process of the information processing apparatus 100 is performed as described above. Note that a reference used to change the display form of the difference information may not be a result of a determination as to whether the supplemental information indicates "Same" or "Different". For example, the difference information generation unit 104 may determine whether a "meaningful difference" exists in the supplemental information and the display controller 105 may change the display form in accordance with a result of the determination. Specifically, the difference information generation unit 104 determines that items in which the difference information is expressed by a binary value have a value "Different", that is, "meaningful difference". On the other hand, the difference information generation unit 104 determines that items which are represented by a difference between values or a matching degree of values have a "meaningful difference" only when the values exceed a predetermined threshold value. As for the items represented by a difference between values, in a case of the item of the inspection date, for example, when a difference between inspection dates is equal to or larger than "5 years", the difference information generation unit 104 determines to be the "meaningful difference". Furthermore, as for the items represented by a matching degree of values, when a matching degree of slice thicknesses is smaller than "25%", the difference information generation unit 104 determines to be the "meaningful difference". In this way, since a display form of the items corresponding to the "meaningful difference" is changed (mainly for an alert display) in the items in which a difference is generated in the supplemental information, the user may recognize only important difference information.

Furthermore, the display form of the individual difference information may be changed in accordance with a degree of a difference in the supplemental information of the individual items (items having a large difference are displayed in an emphasized manner). Furthermore, the user may define importance degrees of the individual items in the supplemental information before the difference information generation unit 104 calculates importance degrees of difference information of the individual items using the importance degrees of the items and degrees of differences. The display controller 105 may differentiate a display form of the difference information in accordance with the degrees. As a method for calculating the importance degrees of the individual difference information, an importance degree of the difference information may be defined by a product of the importance degree of the item and the degree of the difference. As a method for displaying the difference information corresponding to the importance degree, for example, as the importance degree becomes large, the item is displayed in a more emphasized manner (by increasing a display concentration of a character string, for example) and as the importance degree becomes small, the item is displayed in a less emphasized manner (by reducing the display concentration of the character string, for example). Note that the method for changing the display form in accordance with the importance degree is not limited to this and any general method may be employed as long as the display form is changed in accordance with a degree, such as a method for changing color information in accordance with an importance degree.

According to this embodiment, since, in addition to a difference between the two inspection images, a difference between supplemental information which is associated with the difference between the two inspection images is displayed, the user, that is, a doctor, may more appropriately evaluate a difference image.

Modification 1-1

In the first embodiment, the difference image obtaining unit 103 generates a difference image of a difference between the first and second inspection images in step S2030. However, a method for obtaining a difference image is not limited to this. For example, a difference image of the first and second inspection images (which is generated in advance by another apparatus) may be stored in the data server 130 in advance and the difference image obtaining unit 103 may obtain the difference image from the data server 130.

Alternatively, when a difference image has been generated, the difference image obtaining unit 103 may obtain the generated difference image, and only when a difference image has not been generated, the difference image obtaining unit 103 may generate a difference image. Specifically, once a difference image is generated using the first and second inspection images, the difference image obtaining unit 103 stores the difference image in a storage unit, not illustrated, included in the information processing apparatus 100 or the data server 130. Then, in step S2030, the difference image obtaining unit 103 transmits an inquiry indicating whether a difference image of the first and second inspection images exists to the storage unit, not illustrated, in the information processing apparatus 100 or the data server 130. When the determination is affirmative, the difference image obtaining unit 103 obtains the stored difference image. On the other hand, when the determination is negative, the difference image obtaining unit 103 requests the image processing server 140 to perform a process of generating a difference image.

Here, the determination as to whether a difference image exists is made as follows. Specifically, a list of identification information (series IDs, for example) of pairs of inspection images which are sources of the difference image is stored in the storage unit, not illustrated, included in the information processing apparatus 100 or the data server 130. Thereafter, the difference image obtaining unit 103 searches the list for a target difference image using identification information of a pair of the inspection images of the request so that the determination as to whether the target difference image exists is made. Thereafter, in step S2040, the difference information generation unit 104 generates difference information between the supplemental information of the inspection images similarly to the first embodiment. In step S2050, the display controller 105 displays the generated difference information and the stored difference image which is obtained in step S2030 which are associated with each other. In this way, a cost for unnecessary generation of a difference image may be reduced while the effects of the first embodiment are obtained.

Second Embodiment

In the first embodiment, the difference information between the supplemental information of the two inspection images are displayed while being associated with the difference image of the inspection images. On the other hand, in an information processing system according to this embodiment, difference information of supplemental information of two inspection images is recorded and stored in supplemental information of a difference image. By this, the generated difference image may be displayed while the difference information recorded in the supplemental information of the difference image is associated with the difference image without performing a process of extracting the difference information. Accordingly, a cost for generation of difference information unnecessarily performed every time a generated difference image is displayed may be reduced.

FIG. 6 is a diagram illustrating a configuration of the information processing system according to this embodiment. The information processing system includes components the same as those of the first embodiment expect that a representative image determination unit 601 and a supplemental information generation unit 602 are added to an information processing apparatus 600 corresponding to the information processing apparatus 100 of the first embodiment. Furthermore, output from an instruction obtaining unit 101 to a difference image obtaining unit 103 and output from the difference image obtaining unit 103 to an inspection image obtaining unit 102 are additionally performed. Therefore, a number of operations of units included in the information processing apparatus 600 are different from those of the first embodiment. Hereinafter, only portions different from the first embodiment will be described.

The representative image determination unit 601 determines one of first and second inspection images as a representative image. The supplemental information generation unit 602 generates supplemental information of a difference image of the first and second inspection images.

FIG. 7 is a flowchart of an entire processing procedure executed by the information processing apparatus 600. Note that processes in step S7050 and step S7060 in FIG. 7 are the same as those in step S2030 and step S2040 in the flowchart of FIG. 2, and therefore, descriptions thereof are omitted. Hereinafter, only portions different from the flowchart of FIG. 2 will be described.

S7010: Obtainment of Instruction for Selecting Images

In step S7010, the instruction obtaining unit 101 obtains an instruction for selecting images issued by a user from an instruction unit 150. Here, as with the process in step S2010 of FIG. 2, an instruction for selecting the first and second inspection images which are sources of a difference image in an inspection list displayed in a display unit 160 is obtained. Furthermore, when difference images have been generated, an instruction for selecting one of the difference images displayed in an inspection list is obtained.

FIG. 8 is a diagram illustrating an example of display for selecting an image in the inspection list. An inspection list 801 which is similar to the inspection list 301 of FIG. 3 includes inspection images associated with a specific patient. In this embodiment, in addition to the inspection images, generated difference images are displayed in the inspection list. In the inspection list, the difference images are displayed in association with corresponding representative images of first and second inspection images which are generation sources of the difference images.

In the example of FIG. 8, a difference image 802 is displayed in parallel to a CT inspection image 803 (inspection date: Mar. 2, 2017) which is a representative image of two inspection images which are generation sources the difference image 802. This association is realized when supplemental information of a difference image generated by the supplemental information generation unit 602 holds supplemental information of a representative image determined by the representative image determination unit 601 in processes performed in step S7070 and step S7080 described below. By this, the user may reliably recognize an inspection in the inspection list to which the difference image belongs. A case where the difference image 802 of FIG. 8 in the inspection list is selected by the user is illustrated. In this case, a character string of the difference image 802 is displayed in an emphasized manner so that the selection of the difference image 802 is clearly recognized.

S7020: Inspection Image? Difference Image?

In step S7020, the instruction obtaining unit 101 determines whether an instruction for selecting an inspection image has been obtained in step S7010 or an instruction for selecting a difference image has been obtained in step S7010. When it is determined that the instruction for selecting an inspection image has been obtained, information on the instruction for selecting images is output to the inspection image obtaining unit 102. Thereafter the process proceeds to step S7030. On the other hand, when it is determined that the instruction for selecting a difference image has been obtained, information on the instruction for selecting an image is output to the difference image obtaining unit 103. Thereafter the process proceeds to step S7110.

S7030: Obtainment of Inspection Image

In step S7030, the inspection image obtaining unit 102 performs a process the same as that in step S2020 according to the first embodiment. Furthermore, the inspection image obtaining unit 102 outputs the obtained first and second inspection images to the representative image determination unit 601 in this embodiment.

S7040: Generation of Difference Image?

In step S7040, the difference image obtaining unit 103 determines whether a difference image of the obtained first and second inspection images has been generated. When a difference image has not been generated, the process proceeds to step S7050. On the other hand, when a difference image has been generated, the generated difference image is specified and the process proceeds to step S7130. In this case, the determination as to whether a difference image has been generated may be made by a method described in Modification 1-1 of the first embodiment. Alternatively, characteristics of a process in step S7080 described below may be used.

In step S7080, the supplemental information of the difference image holds the supplemental information of the two inspection images which are sources of the difference image, and the difference image is stored in a storage unit, not illustrated, or the data server 130. Thereafter, pairs of identification information of two inspection images described in supplemental information of a large number of generated difference images which have been stored are searched using identification information of the first and second inspection images obtained in this step as a key. By this, the determination as to whether a difference image of the inspection images has been generated may be made or specifying of a difference image which has been generated may be realized. By this method, when compared with the method in Modification 1-1 of the first embodiment, time and effort for storing a list of information on the pairs of two inspection images which are sources of a generated difference image for the storage unit, not illustrated, of the information processing apparatus 600 or the data server 130 may be omitted.

S7050: Obtainment of Difference Image

In step S7050, the difference image obtaining unit 103 performs a process the same as that in step S2030 according to the first embodiment. Furthermore, in this embodiment, the difference image obtaining unit 103 outputs the obtained difference image also to the supplemental information generation unit 602.

S7070: Determination of Representative Image of Inspection Images

In step S7070, the representative image determination unit 601 determines one of the obtained first and second inspection images as a representative image of the two inspection images which is to be associated with the difference image based on a predetermined criterion. On the other hand, the other of the inspection images which is not the representative image is determined as a non-representative image. Then the representative image determination unit 601 outputs the information on the determined representative image to the supplemental information generation unit 602.

As the criterion for determining the representative image, specifically, the representative image determination unit 601 determines one of the first and second inspection images which has a latest imaging date and time with reference to the supplemental information of the first and second inspection images. In interruption of radiogram performed on inspection images by the user, that is, a doctor, a latest image (a current image) is generally a target of the interruption of radiogram and a past image of the same test object is a comparative target. Therefore, the current image is determined as the representative image of the two inspection images which is to be associated with the difference image.

Furthermore, the representative image determination unit 601 may determine an image serving as a reference of positioning when a difference image is generated (a base image) as a representative image. As described in the explanation of the image processing server 140, a difference image is obtained by performing positioning of a comparative image (the first inspection image) to a fixed base image (the second inspection image) and calculating a difference value between the comparative image and the base image which have been subjected to the positioning. Therefore, positions of an anatomical structure of the test object rendered on the image in the difference image and the base image completely correspond to each other. On the other hand, positions of the anatomical structure of the test object in the comparative image and the difference image do not correspond to each other. Accordingly, since the difference image may be determined as a derived image based on the base image, the base image is seen to be suitable for the representative image. Here, in a case where the comparative image (the first inspection image) is a past image and the base image (the second inspection image) is a current image, the second inspection image is determined as a representative image based on any of the criteria described above.

However, in a case where the comparative image (the first inspection image) is a current image and the base image (the second inspection image) is a past image, an inspection image to be determined as a representative image is changed depending on an employed criterion. In this case, one of the criteria is determined as a basic setting (a criteria for determining a latest image as a representative image, for example) in advance, and a setting applied by the user may be changed where appropriate.

In this way, since a representative image of two inspection images which are sources of a difference image is automatically determined based on a predetermined criterion, one of the inspection images to which the difference image belongs may be clearly recognized in an appropriate state without a burden. Note that the user may select a representative image using the instruction unit 150. For example, if two icons corresponding to the first and second inspection images are displayed in the display unit 160 and the user selects one of the displayed icons, the representative image determination unit 601 may determine the selected image as a representative image and the image which has not been selected as a non-representative image.

S7080: Generation of Supplemental Information of Difference Image

In step S7080, the supplemental information generation unit 602 generates supplemental information (third supplemental information) of the difference image based on information on difference information and the representative image and records the generated supplemental information in the obtained difference image. Specifically, the process in step S7080 corresponds to an example of an association unit characterized by associating the difference information with the difference image by recording the difference information in the third supplemental information included in the difference image. Then the supplemental information generation unit 602 stores the difference image which holds the generated supplemental information in the storage unit, not illustrated, and outputs the difference image to the display controller 105. Note that the difference image may be stored in the data server 130.

FIG. 9 is a diagram illustrating examples of items of supplemental information of the difference image and attributes of contents of descriptions. In FIG. 9, an item name 901 of the supplemental information of the difference image is the same as an item name of a general inspection image. Basic information 902 of the supplemental information of the difference image corresponds to supplemental information of a general inspection image. Base image information 903 and comparative image information 904 are supplemental information of the base image (the second inspection image) and the comparative image (the first inspection image), respectively, which are generation sources of the difference image. Difference information 905 represents a difference between the supplemental information of the first inspection image and the supplemental information of the second inspection image. When the supplemental information of the difference image is represented by a DICOM format, the basic information 902 is described as a standard tag and the base image information 903, the comparative image information 904, and the difference information 905 are described as private tags. Content and a format of information stored in the standard tag (a first tag) are defined in advance, and content and a format of information stored in the private tag (a second tag) may be uniquely defined.

As described above, according to this embodiment, the supplemental information of the difference image has a matrix data storage format in which content of four categories, that is, the basic information of the difference information, the supplemental information of the base image and the comparative image, and the difference information, for individual items of the supplemental information are individually described. Here, the supplemental information held by the base image and the supplemental information held by the comparative image are described in the base image information 903 and the comparative image information 904, respectively, for individual item names. Accordingly, all attributes in the base image information 903 and all attributes in the comparative image information 904 are "Base Image" and "Comparative Image", respectively. Furthermore, the difference information generated in step S7060 is described in the difference information 905 for individual item names. Accordingly, attributes of the items of the difference information 905 correspond to properties of the supplemental information generated in step S7060 (Item not to be represented by a numerical value: Binary, Item which may be represented by a numerical value and which has meaning in an absolute difference: Difference between values, and Item which may be represented by a numerical value and which has meaning in a relative difference: Matching degree of values).

Furthermore, the basic information 902 has an attribute of a difference image or a representative image depending on the item name. For example, items of a patient ID, a patient name, and the like are not held by image data of the difference image, and therefore, are the same as content described in items of a patient ID, a patient name, and the like of a representative image which is a source of the difference image. Similarly, an item of an inspection ID is also the same as content described in an item of an inspection ID of the representative image. By this, as described in step S7010, when the inspection list is displayed, the representative image and the difference image may be displayed as inspection images having the same inspection ID.

The series ID is identification information of image data and the difference image is different from the two inspection images, and therefore, a series ID is newly issued to the difference image. Furthermore, items of the number of slices, a thickness of slices, an image size (a horizontal width), an image size (a vertical width), and a pixel interval are information held by image data of the difference image, and therefore, the information obtained from the image data of the difference mage is described. Furthermore, items in which unique information at a time of imaging is described, such as an item of a reconfiguration function is not held by the difference image, and therefore, the item is blank. Note that, when reconfiguration functions of the two inspection images which are sources of the difference image are the same as each other, a name of the reconfiguration functions may be described instead of the blank in the item. Furthermore, even in a case where the reconfiguration functions of the two inspection images are different from each other, a description "Function yyy-Function xxx" may be employed.

Furthermore, an inspection portion may be interpreted into a portion of the test object rendered in the generated difference image. Accordingly, since a region of the difference image is a common region of the two inspection images, portion information of the common region of the inspection portion in base image information and comparative image information is described in an item of the inspection portion in the basic information of the difference image. In a case where content described in the item of the inspection portion in the base image is "TRUNK" and content described in the item of the inspection portion in the comparative image is "CHEST", for example, a range of the trunk is larger than that of the chest and includes the chest. Accordingly, the common region corresponds to the chest, and therefore, "CHEST" is described in the inspection portion of the difference image. In a case where the inspection portion covers a large range of a body, portions having narrow ranges are defined in the inspection portion in advance so that matching between the common region and one of the portions of the narrow ranges may be performed.

For example, portions included in "TRUNK" are defined as follows: "CHEST", "BREAST", "HEART", "STOMACH", "LIVER", "ABDOMEN", "BACK", "SHOULDER", and "FEMORAL REGION". Accordingly, the common region between the "TRUNK" and "CHEST" is determined to "CHEST". Furthermore, in a case where a character string representing the common region may not be easily specified in character strings representing inspection portions, the inspection portion of the difference image may be obtained by performing image processing on at least one of the two inspection images by a general image processing technique so that a portion rendered in the common region is specified. For example, a segmentation process using the probabilistic atlas is performed on one of the two inspection images which has a larger imaging region so that portions (a brain, a lung field, a liver, a heart, a stomach, a large bowel, a backbone, a pelvis, and the like) in the image are extracted. Then one of the portions included in the common region of the inspection images is specified so that an inspection portion of the difference image is obtained.

FIG. 10 is a diagram illustrating examples of items of the supplemental information of the difference image and detailed contents of descriptions. In FIG. 10, reference numerals 1001, 1002, 1003, 1004, and 1005 are information corresponding to the reference numerals 901, 902, 903, 904, and 905, respectively, in FIG. 9. In items of the basic information 1002 to the difference information 1005, detailed contents based on the attributes described in FIG. 9 are described. For example, the attribute of the item of the inspection ID in the basic information 902 of FIG. 9 is "Representative Image". Here, when a criterion for determining a representative image which satisfies "Representative Image=Base image" is employed in step S7070, an inspection ID which is the same as an inspection ID "0002" of the basic image information 1003 is stored in an item of an inspection ID of the basic information 1002 as illustrated in FIG. 10. The same is true on the other items. As illustrated in FIG. 10, since the difference image holds the supplemental information, the information processing apparatus 100 may easily obtain the supplemental information of the base image and the comparative image which are sources of the difference image by only obtaining the difference image and further obtain information on the representative image of the base image and the comparative image. Furthermore, the information processing apparatus 100 may easily obtain difference information between the supplemental information of the base image and the comparative image.

Note that, although the supplemental information of the difference image holds all the supplemental information of the base image and the comparative image in this embodiment, a method for holding the information is not limited to this. For example, only information on a series ID, which is identification information, of the base image and the comparative image may be held by the supplemental information of the difference image, and a target base image or a target comparative image may be searched for using a corresponding series ID as a key where appropriate so that supplemental information of the base image and the comparative image is accessed. Furthermore, information on the inspection date, the imaging date, the modality, and the apparatus manufacturer in the basic information 902 does not belong to image data of the difference image, and therefore, the supplemental information of the representative image is employed. However, as for the items, when the inspection date and the imaging date are replaced by an image generation date, the modality is replaced by an image type, and the apparatus manufacturer is replaced by an image generation manufacturer, unique information which belongs to the image data of the difference image may be employed as below, for example.

Inspection date and imaging date (Image generation date): Mar. 3, 2017 (Generation date of difference image)

Modality (Image type): Subtraction (Difference image)

Apparatus manufacturer (Image generation manufacturer): C company (Manufacturer which generates a difference image)

Furthermore, the unique information of the difference image may additionally include DICOM private tags (an image generation date, an image type, and an image generation manufacturer) in addition to the basic information 902 described as a DICOM standard tag.

S7090: Display Difference Information and Difference Image Associated with Each Other In step S7090, the display controller 105 displays the first and second inspection images obtained from the inspection image obtaining unit 102 in the display unit 160. Furthermore, the display controller 105 displays the difference information obtained from the difference information generation unit 104 which is associated with the difference image obtained from the difference image obtaining unit 103 in the display unit 160. Note that a concrete example of display of the difference information associated with the difference image performed by the display controller 105 is the same as that of the first embodiment.

S7110: Obtainment of Generated Difference Image

In step S7110, the difference image obtaining unit 103 obtains a generated difference image which is stored in the storage unit, not illustrated, or the data server 130 in response to an instruction for selecting the difference image obtained in step S7010. Then the difference image obtaining unit 103 outputs the obtained difference image to the inspection image obtaining unit 102 and the display controller 105.

S7120: Obtainment of Inspection Image Based on Supplemental Information

In step S7120, the inspection image obtaining unit 102 specifies the two inspection images which are generation sources based on the supplemental information of the obtained difference image and obtains the two specified inspection images from the data server 130. Then the inspection image obtaining unit 102 outputs the obtained two inspection images to the display controller 105. In the process in step S7080, the supplemental information of the base image and the supplemental information of the comparative image which are generation sources of the difference image are held by the supplemental information of the difference image. Therefore, the two inspection images may be specified and obtained by accessing the supplemental information of the base image and the supplemental information of the comparative image described in the supplemental information of the difference image. Specifically, series IDs (identification information) of the base image information 1003 and the comparative image information 1004 illustrated in FIG. 10 which are described in the supplemental information of the difference image are obtained. Then the inspection images are obtained from the data server 130 using the obtained two series IDs as keys. In this way, since the supplemental information of the difference image holds the supplemental information of the two inspection images, when the difference image is obtained, the inspection images which are sources of the difference image may be simultaneously obtained.

Note that, in step S7120, character strings of the specified inspection images may be displayed in an emphasized manner so that it is easily recognized in the inspection list of FIG. 8 that the two inspection images have been specified. For example, when the CT inspection image 804 corresponding to the inspection date of Oct. 25, 2014 is specified as a non-representative image (=a comparative image) in addition to the CT inspection image 803 corresponding to the inspection date of Mar. 2, 2017 to which the difference image belongs, emphasis display is performed as follows. Specifically, character strings of the CT inspection image 803 and the CT inspection image 804 are displayed in an emphasized manner. When selecting the difference image 802, the user may easily recognize the two inspection images which are generation sources of the difference image 802.

S7130: Obtainment of Generated Difference Image

In step S7130, the difference image obtaining unit 103 obtains the generated difference image specified in step S7040. An obtaining method is the same as that in step S7110, and therefore, a description thereof is omitted. The difference image obtaining unit 103 outputs the generated difference image which has been obtained to the display controller 105. In this way, when the difference image has been generated, a cost for unnecessary generation of a difference image may be reduced.

The process of the information processing apparatus 600 is performed as described above. As described above, in a case where the difference image which has been generated once is displayed, when the user selects the first and second inspection images in step S7010, the process proceeds from step S7020 to step S7030. Furthermore, the process proceeds from step S7040 to step S7130 where the generated difference image is obtained before the difference image recorded in the supplemental information of the difference image is read and displayed in association with the difference image in step S7090. On the other hand, when the user selects the difference image in step S7010, the process proceeds from step S7020 to step S7110 where the generated difference image is obtained before the same display is performed in step S7090. Accordingly, when the generated difference image is displayed, a cost for generating the difference information in step S7060 may be reduced.

According to this embodiment, since the difference information of the supplemental information of the two inspection images is recorded and stored in the supplemental information of the difference image, when the difference image is displayed again, the difference information recorded in the supplemental information of the difference image may be read and displayed in association with the difference image. Accordingly, a cost for generation of unnecessary difference information performed every time a generated difference image is displayed may be reduced.

Third Embodiment

In the first embodiment, the information processing apparatus 100 displays the difference information of the supplemental information of the first and second inspection images which are sources of the difference image. By this, the user observes the number of items in which a difference is generated and degrees of the differences in the difference information so as to qualitatively evaluate quality of the difference image. On the other hand, according to this embodiment, an information processing apparatus automatically calculates and displays a degree of reliability in accordance with the number of items in which a difference is generated and degrees of the differences in difference information. By this, a user may check quantitative quality of a difference image which is useful for interpretation of radiogram using the difference image.

FIG. 11 is a diagram illustrating a configuration of an information processing system according to this embodiment. The configuration is the same as that of the information processing apparatus 100 in the first embodiment except that a reliability calculation unit 1101 is additionally provided. Hereinafter, only portions different from the first embodiment will be described.

The reliability calculation unit 1101 calculates a degree of reliability of a difference image based on difference information of supplemental information of two inspection images which are sources of the difference image.

FIG. 12 is a flowchart of an entire processing procedure executed by an information processing apparatus 1100. Note that, in FIG. 12, processes in step S11010, step S11020, step S11030, and step S11040 are the same as the process in the following steps in the flowchart of FIG. 2. Specifically, the processes in step S11010, step S11020, step S11030, and step S11040 are the same as the process in step S2010, step S2020, step S2030, and step S2040, respectively. Therefore, descriptions of the same processes are omitted. Hereinafter, only portions different from the flowchart of FIG. 2 will be described.

S11050: Calculation of Degree of Reliability of Difference Image Based on Difference Information In step S11050, the reliability calculation unit 1101 calculates a degree of reliability of a difference image based on obtained difference information. Then the reliability calculation unit 1101 outputs the calculated reliability degree to a display controller 105. Specifically, the process in step S11050 corresponds to an example of a calculation unit which calculates a reliability degree of a difference image based on difference information. Hereinafter, a method for calculating a reliability degree will be described in detail. In this embodiment, the reliability calculation unit 1101 calculates a reliability degree in accordance with the number of items in which a difference is generated between supplemental information and degrees of the differences. Specifically, the reliability calculation unit 1101 calculates a reliability degree S using the following expression.

[Math. 1]

$$S = \frac{\sum_{i=1}^{N} w_i M_i}{\sum_{i=1}^{N} w_i} \quad (3)$$

Here, "i" denotes an item number of difference information and "N" denotes the number of items of the difference information (1 less than or equal to i less than or equal to N). It is assumed here that, one of items essentially indicating the same information, such as a patient ID and a patient name, is set as a target of calculation based on Expression (3) and the other is not a target of the calculation. Furthermore, "$w_i$" denotes a weight of an i-th item of the difference information ($w_i$ greater than or equal to 0). A value of "$w_i$" is determined in advance for each item number i, and as a degree of influence of an item of the difference information on quality of the difference image is larger, a larger weight value is set, and as the degree is smaller, a smaller value is set. Specifically, this calculation corresponds to an example of a calculation unit characterized by calculating a reliability degree of a difference image based on the number of items in which a difference is generated in the difference information and a degree of the difference for each item. Furthermore, this calculation corresponds to an example of the calculation unit characterized by calculating a reliability degree of a difference image based on a weight set for each item.

For example, if patient IDs (patient names) are different from each other, two different inspection images which are sources of a difference image are obtained by capturing different patients, and therefore, anatomical structures in the images are considerably different from each other. Therefore, influence of the difference of this item on the quality of the difference image is large. Furthermore, if contents in the item of the modality are different from each other, properties of information on the inspection images are totally different from each other, and therefore, the quality is considerably affected. Accordingly, the reliability calculation unit 1101 sets a large value in the weight $w_i$ ($wd_i$=10, for example) for such an item. On the other hand, when apparatus manufacturers are different from each other, attributes of images vary more or less depending on a manufacturer. However, if the modalities are the same, main image attributes are the same, and therefore, images are fundamentally not different from each other in a large degree. Therefore, influence on the quality is a middle class. Accordingly, the reliability calculation unit 1101 sets a middle value in the weight $w_i$ ($w_i$=5, for example) for such an item. Furthermore, the reliability calculation unit 1101 sets 0 to the weight $w_i$ for an item in which the difference information does not affect the quality of the difference image.

Furthermore, "$M_i$" indicates a matching degree (0) less than or equal to $M_i$ less than or equal to 1) between supplemental information in the i-th item of the difference information. The difference information is categorized into the following three types: (A) Difference information represented by a binary value, (B) Difference information represented by a difference between values, and (C) Difference information represented by a matching degree of values. As for (A), a value of supplemental information of the difference information may be only represented by "Same" or "Different", and therefore, the difference information is represented by a matching degree $M_i$ of 1 (the same) or 0 (different). When the difference information of the item of the modality indicates "Same", $M_i$ is 1 and when the difference information indicates "Different", $M_i$ is 0. As for (C), a matching degree M of the values calculated in step S2040 according to the first embodiment is employed as the matching degree $M_i$ for each item. As for (B), the difference information indicates a difference between values of the item, and therefore, the difference information is not included in a range from 0 to 1. For example, when the difference information of an item of an inspection date indicates "2 years 4 months and 5 days", "2 years 4 months and 5 days" which corresponds to "859" days exceeds a value 1. Therefore, the following expression is employed.

[Math. 2]

$$M_i = 1 - \frac{D_i}{C + D_i} \quad (4)$$

Here, "$D_i$" denotes a difference between values of an item and "C" denotes a constant. It is assumed here that C is 365. When the difference information on a difference between inspection dates is 0 days (Same) ($D_i$=0), $M_i$ is 1.0. As the difference information (Di) on a difference between the inspection dates becomes large, a value of $M_i$ becomes close to 0 without limit. Furthermore, when the difference information on a difference between the inspection dates is 1 year flat, that is, 365 days ($D_i$=365), $M_i$ is 0.5. In the example described above, $D_i$ is 859, and as a result of Expression (4), $M_i$ is 0.29. In this way, the reliability calculation unit 1101 calculates a reliability degree S of a difference image.

S11060: Display Difference Image and Reliability Degree Associated with Each Other In step S11060, a display controller 105 displays first and second inspection images obtained from an inspection image obtaining unit 102 in a display unit 160. Furthermore, the display controller 105 displays information on the reliability degree S obtained from the reliability calculation unit 1101 in the display unit 160 in association with a difference image obtained from a difference image obtaining unit 103. Here, a method for displaying the two inspection images and the difference image is the same as that in step S2050 in the first embodiment, and therefore, a description thereof is omitted. In this embodiment, the display controller 105 further displays the reliability degree S in an inside or in the vicinity of a tomographic image 503 of the difference image illustrated in FIG. 5, for example, in association with the difference image.

FIG. 13 is a diagram illustrating an example of display of association between a reliability degree and a difference image. A reference numeral 1301 in FIG. 13 indicates a reliability degree of the difference image and other displayed items are the same as those in FIG. 5. In this example, the reliability degree 1301 is displayed inside the difference image. Accordingly, the user may easily recognize the reliability degree of the difference image being observed. Note that the difference information 512 in the tomographic image 503 and the difference information list 504 displayed in the first embodiment may be displayed or may not be displayed. Alternatively, one of the difference information 512 and the difference information list 504 may be displayed (for example, the difference information 512 is displayed but the difference information list 504 is not displayed. The process of the information processing apparatus 1100 is performed as described above.

According to this embodiment, the user may quantitatively recognize quality of the difference image by automatically calculating and displaying a reliability degree in accordance with the number of items in which a difference is generated and degrees of the differences in the difference information, which is useful for interruption of radiogram using the difference image.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-108241, filed May 31, 2017, which is hereby incorporated by reference herein in its entirety.

The invention claimed is:

1. An information processing apparatus comprising:
an image obtaining unit configured to obtain a first inspection image having first supplemental information and a second inspection image having second supplemental information, wherein the first supplemental information is information relating to at least one of first imaging parameters and first reconstruction parameters related to the first inspection image and to be added when the first inspection image is captured or generated, and the second supplemental information is information relating to at least one of second imaging parameters and second reconstruction parameters related to the second inspection image and to be added when the second inspection image is captured or generated;
a difference image obtaining unit configured to obtain a difference image generated using the first and second inspection images;
a difference information obtaining unit configured to obtain difference information on a difference between the first supplemental information and the second supplemental information; and
an association unit configured to associate the difference information with the difference image,
wherein the association unit associates the difference information with the difference image by recording the difference information in third supplemental information included in the difference image, and
wherein the third supplemental information includes a first tag defined in advance and a second tag uniquely defined, and the association unit records the difference information in the second tag included in the third supplemental information.

2. The information processing apparatus according to claim 1, further comprising a display control unit configured to display the difference information and the difference image which are associated with each other in a display unit.

3. The information processing apparatus according to claim 2, wherein the display control unit displays the associated difference information such that the difference information is superposed on the difference image.

4. The information processing apparatus according to claim 2,
wherein each of the first supplemental information and the second supplemental information includes at least one item, and
wherein the difference information is obtained by obtaining differences between items of the first supplemental information and corresponding items of the second supplemental information.

5. The information processing apparatus according to claim 4,
wherein the display control unit further displays at least one of the items of the first supplemental information and of the second supplemental information, and
wherein the display control unit displays the difference information corresponding to a displayed item and the difference image.

6. The information processing apparatus according to claim 5, wherein the display control unit displays a list of the difference information corresponding to the items which are not being displayed.

7. The information processing apparatus according to claim 4,
wherein the first supplemental information includes at least an item indicating a first obtaining date when the first inspection image is obtained,
wherein the second supplemental information includes at least an item indicating a second obtaining date when the second inspection image is obtained, and
wherein the difference information includes at least a difference between the first and second obtaining dates.

8. The information processing apparatus according to claim 4, wherein the display control unit differentiates a display form of the item in which a difference is generated from a display form of an item in which a difference is not generated.

9. The information processing apparatus according to claim 8, wherein the display control unit does not display the difference information of the item in which a difference is not generated.

10. The information processing apparatus according to claim 4, wherein the display control unit differentiates display forms of the difference information of the items in accordance with degrees of influence of the differences of the items on the difference image.

11. The information processing apparatus according to claim 1, wherein the association unit generates the third supplemental information and records the difference information in the third supplemental information.

12. The information processing apparatus according to claim 1
wherein the imaging parameters are parameters that include information on at least one of an imaging state and a body position, and
wherein the reconstruction parameters are parameters that include information on at least one of a reconfiguration function and a slice thickness.

13. The information processing apparatus according to claim 1
wherein the image obtaining unit further obtains imaging date and time and inspection date and time as supplemental information.

14. A method for controlling an information processing apparatus, the method comprising:
obtaining a first inspection image having first supplemental information and a second inspection image having second supplemental information, wherein the first supplemental information is information relating to at least one of first imaging parameters and first reconstruction parameters related to the first inspection image and to be added when the first inspection image is captured or generated, and the second supplemental information is information relating to at least one of second imaging parameters and second reconstruction parameters related to the second inspection image and to be added when the second inspection image is captured or generated;
obtaining a difference image generated using the first and second inspection images;
obtaining difference information on a difference between the first supplemental information and the second supplemental information; and
associating the difference information with the difference image by recording the difference information in third supplemental information included in the difference image,
wherein the third supplemental information includes a first tag defined in advance and a second tag uniquely defined, and the association unit records the difference information in the second tag included in the third supplemental information.

15. An information processing apparatus comprising:
an image obtaining unit configured to obtain a first inspection image having first supplemental information and a second inspection image having second supplemental information, wherein the first supplemental information is information relating to at least one of first imaging parameters and first reconstruction parameters related to the first inspection image and to be added when the first inspection image is captured or generated, and the second supplemental information is information relating to at least one of second imaging parameters and second reconstruction parameters related to the second inspection image and to be added when the second inspection image is captured or generated;
a difference image obtaining unit configured to obtain a difference image generated using the first and second inspection images;
a difference information obtaining unit configured to obtain difference information on a difference between the first supplemental information and the second supplemental information;
a calculation unit configured to calculate a degree of reliability of the difference image based on the difference information; and
a display control unit configured to display information on the degree of reliability and the difference image which are associated with each other in a display unit,
wherein each of the first supplemental information and the second supplemental information includes at least one item,
wherein the difference information is obtained by obtaining differences between items of the first supplemental information and corresponding items of the second supplemental information, and
wherein the calculation unit calculates the degree of reliability of the difference image based on the number of items in which a difference is generated and which are included in the difference information and degrees of differences for individual items.

16. The information processing apparatus according to claim 15, wherein the calculation unit further calculates the degree of reliability of the difference image based on weights set for individual items.

17. The information processing apparatus according to claim 15, wherein the display control unit displays, in a display unit, information on the degree of reliability and the difference image which are associated with each other by superposing information on the degree of reliability on the difference image.

18. A method for controlling an image processing apparatus, the method comprising:
obtaining a first inspection image having first supplemental information and a second inspection image having second supplemental information, wherein the first supplemental information is information relating to at least one of first imaging parameters and first reconstruction parameters related to the first inspection image and to be added when the first inspection image is captured or generated, and the second supplemental information is information relating to at least one of second imaging parameters and second reconstruction parameters related to the second inspection image and to be added when the second inspection image is captured or generated;
obtaining a difference image generated using the first and second inspection images;
obtaining difference information on a difference between the first supplemental information and the second supplemental information;
calculating a degree of reliability of the difference image based on the difference information; and
displaying information on the degree of reliability and the difference image which are associated with each other in a display unit,
wherein each of the first supplemental information and the second supplemental information includes at least one item,
wherein the difference information is obtained by obtaining differences between items of the first supplemental information and corresponding items of the second supplemental information, and
wherein the degree of reliability of the difference image is calculated based on the number of items in which a difference is generated and which are included in the difference information and degrees of differences for individual items.

* * * * *